US012636264B2

(12) United States Patent
Zhou et al.

(10) Patent No.: US 12,636,264 B2
(45) Date of Patent: May 26, 2026

(54) METHODS AND MATERIALS FOR DIAGNOSIS AND TREATMENT OF NEURONAL DISORDER

(71) Applicant: Genemo, Inc., San Diego, CA (US)

(72) Inventors: Zixu Zhou, San Diego, CA (US);
Qiuyang Wu, San Diego, CA (US);
Sheng Zhong, San Diego, CA (US);
Zhangming Yan, San Diego, CA (US)

(73) Assignee: Genemo, Inc., San Diego, CA (US)

( * ) Notice: Subject to any disclaimer, the term of this patent is extended or adjusted under 35 U.S.C. 154(b) by 916 days.

(21) Appl. No.: 17/802,908

(22) PCT Filed: Feb. 26, 2021

(86) PCT No.: PCT/US2021/019859
§ 371 (c)(1),
(2) Date: Aug. 26, 2022

(87) PCT Pub. No.: WO2021/173962
PCT Pub. Date: Sep. 2, 2021

(65) Prior Publication Data
US 2023/0201136 A1     Jun. 29, 2023

Related U.S. Application Data

(60) Provisional application No. 62/983,569, filed on Feb. 28, 2020.

(51) Int. Cl.
*A61K 31/13*     (2006.01)
*A61P 25/28*     (2006.01)
(52) U.S. Cl.
CPC .............. *A61K 31/13* (2013.01); *A61P 25/28* (2018.01)
(58) Field of Classification Search
CPC ...... A61K 31/13; A61K 38/443; A61K 45/06; A61P 25/28; C12Y 101/01095; C12N 9/0006
See application file for complete search history.

(56) References Cited

U.S. PATENT DOCUMENTS

| | | | |
|---|---|---|---|
| 6,673,908 B1 * | 1/2004 | Stanton, Jr. | ........ C07K 14/7151 435/6.16 |
| 10,151,761 B2 | 12/2018 | Arnoldussen et al. | |
| 10,527,632 B2 | 1/2020 | Bahn et al. | |
| 2014/0322734 A1 * | 10/2014 | Rai | .................... G01N 33/6896 422/69 |
| 2016/0154011 A1 * | 6/2016 | Lovestone | ......... G01N 33/6896 435/7.92 |
| 2018/0105508 A1 * | 4/2018 | Sabatini | .................. A61K 45/06 |
| 2018/0142007 A1 | 5/2018 | Novak et al. | |
| 2019/0071400 A1 * | 3/2019 | Mainolfi | .............. C07D 413/12 |
| 2020/0124624 A1 | 4/2020 | Sardi et al. | |

OTHER PUBLICATIONS

Arafah et al., The Future of Precision Medicine in the Cure of Alzheimer's Disease. Biomedicines, 11(2), 335 (Year: 2023).*
Pankevich DE, Altevogt BM, Dunlop J, Gage FH, Hyman SE. Improving and accelerating drug development for nervous system disorders. Neuron. Nov. 5, 2014;84(3):546-53. doi: 10.1016/j.neuron. 2014.10.007. Epub Nov. 5, 2014. (Year: 2014).*
Paterson et al. A targeted proteomic multiplex CSF assay identifies increased malate dehydrogenase and other neurodegenerative biomarkers in individuals with Alzheimer's disease pathology. Transl Psychiatry 6, e952 (2016). https://doi.org/10.1038/tp.2016.194 (Year: 2016).*
Sasabe et al., The EMBO Journal (2007) 26, 4149-4159. (Year: 2007).*
Rabipour et al., bioRxiv 2019.12.11.871681; doi: https://doi.org/10.1101/2019.12.11.871681 (Year: 2019).*
Zhou, et al., Extracellular RNA in a single droplet of human serum reflects physiologic and disease states, Proc. Natl. Acad. Sci. U.S.A. 116 (38) 19200-19208, https://doi.org/10.1073/pnas.1908252116 (2019). (Year: 2019).*
International Search Report in PCT/US2021/019859 mailed on May 13, 2021, 4 pages.
Written Opinion in PCT/US2021/019859 mailed on May 13, 2021, 9 pages.
RW Paterson et al., A Targeted Proteomic Multiplex CSF Assay Identifies Increased Malate Dehydrogenase and Other Neurodegenerative Biomarkers in Individuals with Alzheimer's Disease Pathology, Translational Psychiatry, 6: 1-10, 2016.
Enders K.O. NG et al., Presence of Filterable and Nonfilterable mRNA in the Plasma of Cancer Patients and Healthy Individuals, Clinical Chemistry, 48(8): 1212-1217, 2002.
Enders K.O. NG et al., mRNA of Placental Origin is Readily Detectable in Maternal Plasma, PNAS, 100(6): 4748-4753, 2003.
José Miguel García et al., Extracellular Plasma RNA from Colon Cancer Patients is Confined in a Vesicle-like Structure and is mRNA-Enriched, RNA, 14: 1424-1432, 2008.
Jane E. Freedman et al., Diverse Human Extracellular RNAs are Widely Detected in Human Plasma, Nature Communications, 7: 1-13, 2016.
Ashish Yeri et al., Total Extracellular Small RNA Profiles from Plasma, Saliva, and Urine of Healthy Subjects, Scientific Reports, 7: 1-13, 2017.
Yuan, Tiezheng et al., Plasma Extracellular RNA Profiles in Healthy and Cancer Patients, Scientific Reports, 6: 1-11, 2016.
Oscar D. Murillo et al., exRNA Atlas Analysis Reveals Distinct Extracellular RNA Cargo Types and Their Carriers Present across Human Biofluids, Cell, 177: 463-477.e415, 2019.
Kasandra Burgos et al., Profiles of Extracellular miRNA in Cerebrospinal Fluid and Serum from Patients with Alzheimer's and Parkinson's Diseases Correlate with Disease Status and Features of Pathology, PLoS One, 9(5): 1-20, 2014.

(Continued)

*Primary Examiner* — James H Alstrum-Acevedo
*Assistant Examiner* — Chantal Adlam
(74) *Attorney, Agent, or Firm* — METIS IP LLC

(57)     ABSTRACT

Provided herein are methods of managing, preventing, or treating a neuronal disorder in a subject, such as Alzheimer's disease, comprising monitoring the expression level of phosphoglycerate dehydrogenase (PHGDH) in the subject over an observation period of time, and administering to the subject an effective amount of a therapy for managing, preventing or treating the neuronal disorder.

16 Claims, 14 Drawing Sheets

Figure 1:
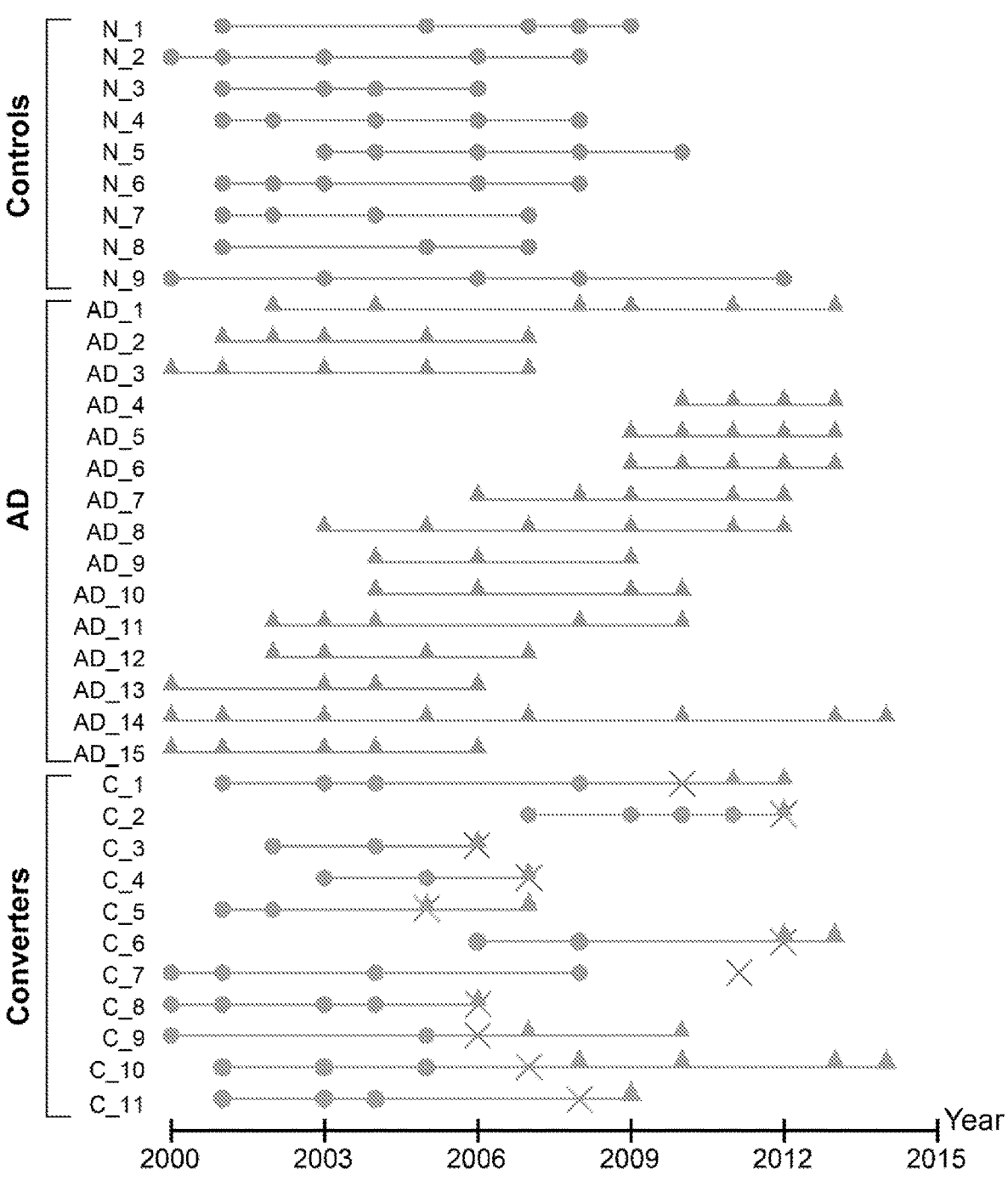

Specification includes a Sequence Listing.

(56)                References Cited

OTHER PUBLICATIONS

Min Young Lee et al., Distinct Profiles of Cell-Free MicroRNAs in Plasma of Veterans with Post-Traumatic Stress Disorder, Journal of Clinical Medicine, 8: 1-16, 2019.

Srimeenakshi Srinivasan et al., Small RNA Sequencing across Diverse Biofluids Identifies Optimal Methods for exRNA Isolation, Cell, 177: 446-462.e16, 2019.

Zhou, Zixu et al., Extracellular RNA in a Single Droplet of Human Serum Reflects Physiologic and Disease States, PNAS, 116(38): 19200-19208, 2019.

James T. Yurkovich et al., Blood Is a Window into Health and Disease, Clinical Chemistry, 65(10): 1-3, 2019.

Fatemeh Momen-Heravia et al., Increased Number of Circulating Exosomes and Their MicroRNA Cargos are Potential Novel Biomarkers in Alcoholic Hepatitis, Journal of Translational Medicine, 13: 1-13, 2015.

Klaas E. A. Max et al., Human Plasma and Serum Extracellular Small RNA Reference Profiles and Their Clinical Utility, PNAS, 1-10, 2018.

Fabienne Kunz et al., Detection of AML-Specific Mutations in Pediatric Patient Plasma Using Extracellular Vesicle-derived RNA, Annals of Hematology, 2019, 9 pages.

David P. Farrington, Longitudinal Research Strategies: Advantages, Problems, and Prospects, Journal of the American Academy of Child & Adolescent Psychiatry, 30(3): 369-374, 1991.

Chen, Rui et al., Longitudinal Personal DNA Methylome Dynamics in a Human with a Chronic Condition, Nature Medicine, 2018, 10 pages.

Chao, Jiang et al., Dynamic Human Environmental Exposome Revealed by Longitudinal Personal Monitoring, Cell, 175: 277-291. e31, 2018.

Zhou, Wenyu et al., Longitudinal Multi-omics of Host-microbe Dynamics in Prediabetes, Nature, 569: 663-671, 2019.

Juan Pablo Lopez et al., MicroRNAs 146a/b-5 and 425-3p and 24-3p are Markers of Antidepressant Response and Regulate MAPK/ Wnt-system Genes, Nature Communications, 8: 1-12, 2017.

Oliver Preische et al., Serum Neurofilament Dynamics Predicts Neurodegeneration and Clinical Progression in Presymptomatic Alzheimer's Disease, Nature Medicine, 2019, 7 pages.

Akinori Nakamura et al., High Performance Plasma Amyloid-β Biomarkers for Alzheimer's Disease, Nature, 1-6, 2018.

Mehtap Bacioglu et al., Neurofilament Light Chain in Blood and CSF as Marker of Disease Progression in Mouse Models and in Neurodegenerative Diseases, Neuron, 91: 1-11, 2016.

Philip S.J. Weston et al., Serum Neurofilament Light in Familial Alzheimer Disease, Neurology, 89 (21): 1-9, 2017.

Lin, Yung-Shuan et al., Levels of Plasma Neurofilament Light Chain and Cognitive Function in Patients with Alzheimer or Parkinson Disease, Scientific Reports, 8: 1-8, 2018.

Niklas Mattsson et al., Association of Plasma Neurofilament Light With Neurodegeneration in Patients With Alzheimer Disease, JAMA Neurology, E1-E10, 2017.

Andréea L. Benedet et al., Plasma Neurofilament Light Associates with Alzheimer's Diseasemetabolic Decline in Amyloid-positive Individuals, Alzheimer's & Dementia, 11: 679-689, 2019.

Jia, Longfei et al., Concordance Between the Assessment of Aβ42, T-tau, and P-T181-tau in Peripheral Blood Neuronal-derived Exosomes and Cerebrospinal Fluid, Alzheimer's & Dementia, 15: 1071-1080, 2019.

Suzanne E. Schindler, High-precision Plasma β-amyloid 42/40 Predicts Current and Future Brain Amyloidosis, Neurology, 1-13, 2019.

Carine Z. J. Lim et al., Subtyping of Circulating Exosome-bound Amyloid β Reflects Brain Plaque Deposition, Nature Communications, 10: 1-11, 2019.

Eric M. Reiman et al., Alzheimer's Prevention Initiative: A Plan to Accelerate the Evaluation of Presymptomatic Treatments, Journal of Alzheimer's Disease, 2011, 12 pages.

Giovanni B. Frisoni et al., Strategic Roadmap for an Early Diagnosis of Alzheimer's Disease Based on Biomarkers, Lancet Neurol, 16: 661-676, 2017.

Dimitrios Kapogiannis et al., Association of Extracellular Vesicle Biomarkers With Alzheimer Disease in the Baltimore Longitudinal Study of Aging, JAMA Neurology, E1-E12, 2019.

Nina Silverberg et al., NIA Commentary on the NIA-AA Research Framework: Towards a Biological Definition of Alzheimer's Disease, Alzheimer's & Dementia, 14: 576-578, 2018.

Mariet Allen et al., Conserved Brain Myelination Networks are Altered in Alzheimer's and Other Neurodegenerative Diseases, Alzheimer's & Dementia, 1-15, 2017.

Reisa A. Sperling et al., The A4 study: stopping AD before symptoms begin? Science Translational Medicine, 6 (228): 1-3, 2014.

Ben Readhead et al., Multiscale Analysis of Independent Alzheimer's Cohorts Finds Disruption of Molecular, Genetic, and Clinical Networks by Human Herpesvirus, Neuron, 99: 64-82.e7, 2018.

Winnie S. Liang et al., Altered Neuronal Gene Expression in Brain Regions Differentially Affected by Alzheimer's Disease: a Reference Data Set, Physiol Genomics, 33: 240-256, 2008.

Wang, Shu et al., Gene Expression Profiling in Alzheimer's Disease Brain Microvessels, Journal of Alzheimer's Disease, 31: 193-205, 2012.

Hamel Patel et al., A Meta-Analysis of Alzheimer's Disease Brain Transcriptomic Data, Journal of Alzheimer's Disease, 1-22, 2019.

Hansruedi Mathys et al., Single-cell Transcriptomic Analysis of Alzheimer's Disease, Nature, 2019, 6 pages.

Rose Ann Huynh et al., Alzheimer's Disease: Biomarkers in the Genome, Blood, and Cerebrospinal Fluid, Frontiers in Neurology, 8: 1-15, 2017.

Guo, Caiwei et al., Tau Activates Transposable Elements in Alzheimer's Disease, Cell Reports, 23: 2874-2880, 2018.

Li, Wanhe et al., Activation of Transposable Elements During Aging and Neuronal Decline in Drosophila, Nature Neuroscience, 1-4, 2013.

Li, Wanhe et al., Transposable Elements in TDP-43-Mediated Neurodegenerative Disorders, PLoS One, 7(9): 1-10, 2012.

Sun, Wenyan et al., Pathogenic Tau-induced pIRNA Depletion Promotes Neuronal Death Through Transposable Element Dysregulation in Neurodegenerative Tauopathies, Nature Neuroscience, 2018, 13 pages.

Janet Piñero et al., The DisGeNET knowledge platform for disease genomics: 2019 update, Nucleic Acids Research, 48: D845-D855, 2020.

Shahar Barbash et al., Alzheimer's Brains Show Inter-related Changes in RNA and Lipid Metabolism, Neurobiology of Disease, 2017, 28 pages.

Naoyuki Sato et al., The Roles of Lipid and Glucose Metabolism in Modulation of β-Amyloid, Tau, and Neurodegeneration in the Pathogenesis of Alzheimer Disease, Frontiers in Aging Neuroscience, 7: 1-9, 2015.

Richard J. Hodes et al., Accelerating Medicines Partnership: Alzheimer's Disease (AMP-AD) Knowledge Portal Aids Alzheimer's Drug Discovery through Open Data Sharing, Expert Opinion on Therapeutic Targets, 1-3, 2016.

Philip L. De Jager et al., A Multi-omic Atlas of the Human Frontal Cortex for Aging and Alzheimer's Disease Research, Scientific Data, 5: 1-13, 2018.

Robert Y. Yang et al., A Systematic Survey of Human Tissue-specific Gene Expression and Splicing Reveals New Opportunities for Therapeutic Target Identification and Evaluation, bioRxiv, 2018, 39 pages.

David C. Hondius et al., Profiling the Human Hippocampal Proteome at all Pathologic Stages of Alzheimer's Disease, Alzheimer's & Dementia, 1-15, 2016.

Nicholas T. Seyfried et al., A Multi-network Approach identifies Protein-Specific Co-expression in Asymptomatic and Symptomatic Alzheimer's Disease, Cell Systems, 4: 1-13, 2017.

Ping, Lingyan et al., Global Quantitative Analysis of the Human Brain Proteome in Alzheimer's and Parkinson's Disease, Scientific Data, 5: 1-12, 2018.

Jason C. H. Tsang et al., Integrative Single-cell and Cell-free Plasma RNA Transcriptomics Elucidates Placental Cellular Dynamics, PNAS, 1-10, 2017.

(56)                References Cited

OTHER PUBLICATIONS

Martina Absinta et al., Human and Nonhuman Primate Meninges Harbor Lymphatic Vessels That Can Be Visualized Noninvasively by MRI, Elife, 1-15, 2017.

Sandro Da Mesquita et al., Functional Aspects of Meningeal Lymphatics in Ageing and Alzheimer's Disease, Nature, 2018, 7 pages.

Lydia Alvarez-Erviti et al., Delivery of siRNA to the Mouse Brain by Systemic Injection of Targeted Exosomes, Nature Biotechnology, 29(4): 341-345, 2011.

Harm J. Van De Haar et al., Blood-Brain Barrier Leakage in Patients with Early Alzheimer Disease, Radiology, 1-9, 2016.

Melanie D. Sweeney et al., Blood-brain Barrier Breakdown in Alzheimer Disease and Other Neurodegenerative Disorders, Nature Reviews Neurology, 1-18, 2018.

Chen, Xu-Qiao et al., Alzheimer Disease Pathogenesis: Insights From Molecular and Cellular Biology Studies of Oligomeric Aβ and Tau Species, Frontiers in Neuroscience, 13: 1-21, 2019.

Jung Hoon Yang et al., Brain-specific Phgdh Deletion Reveals a Pivotal Role for L-serine Biosynthesis in Controlling the Level of D-serine, an N-methyl-D-aspartate Receptor Co-agonist, in Adult Brain, The Journal of Biological Chemistry, 285(53): 41380-41390, 2010.

Zhu, Shujia et al., Mechanism of NMDA Receptor Inhibition and Activation, Cell, 165: 1-11, 2016.

Matildé Le Bail et al., Identity of the NMDA Receptor Coagonist is Synapse Specific and Developmentally Regulated in the Hippocampus, PNAS, 1-10, 2015.

Matthew R. Hynd et al., Glutamate-mediated Excitotoxicity and Neurodegeneration in Alzheimer's Disease, Neurochem international, 45: 583-595, 2004.

Jeffrey T. Ehmsen et al., D-Serine in Glia and Neurons Derives from 3-Phosphoglycerate Dehydrogenase, The Journal of Neuroscience, 33(30): 12464-12469, 2013.

Atsushi Hashimoto et al., Endogenous D-Serine in Rat Brain: N-Methyl-D-Aspartate Receptor-Related Distribution and Aging, Journal of Nnirochemulry, 60(2): 783-786, 1993.

Hiroshi Katsuki et al., Contribution of Endogenous Glycine and D-serine to Excitotoxic and Ischemic Cell Death in Rat Cerebrocortical Slice Cultures, Life Sciences, 81(9): 740-749, 2007.

Jumpei Sasabe et al., D-serine is a Key Determinant of Glutamate Toxicity in Amyotrophic Lateral Sclerosis, The EMBO Journal, 26(18): 4149-4159, 2007.

Enmanuel J. Perez et al., Enhanced Astrocytic D-serine Underlies Synaptic Damage After Traumatic Brain Injury, The Journal of Clinical Investigation, 127(8): 3114-3125, 2017.

C Madeira et al., D-serine Levels in Alzheimer's Disease: Implications for Novel Biomarker Development, Translational Psychiatry, 5: 1-9, 2015.

Asif K. Mustafa et al., Serine Racemase Deletion Protects Against Cerebral Ischemia and Excitotoxicity, The Journal of Neuroscience, 30(4): 1413-1416, 2010.

Jumpei Sasabe et al., D-Amino Acid Oxidase Controls Motoneuron Degeneration Through D-Serine, PNAS, 109(2): 627-632, 2012.

Benedikt Zott et al., A Vicious Cycle of β Amyloid-dependent Neuronal Hyperactivation, Science, 365: 559-565, 2019.

Andrea Witt et al., Memantine Hydrochloride, Nature Reviews, Drug Discovery, 3: 109-110, 2004.

Rupert Mcshane et al., Memantine for Dementia, Cochrane Database of Systematic Reviews, 2019, 296 pages.

Li, Wenxue et al., Human Endogenous Retrovirus-K Contributes to Motor Neuron Disease, Science Translational Medicine, 7(307): 1-12, 2015.

Elaine Y. Liu et al., Loss of Nuclear TOP-43 Is Associated with Decondensation of LINE Retrotransposons, Cell Reports, 27: 1409-1421, 2019.

D.T. Balu, The NMDA Receptor and Schizophrenia: From Pathophysiology to Treatment, Advances in Pharmacology, 76: 351-382, 2016.

Alida Spalloni et al., Role of the N-methyl-d-aspartate Receptors Complex in Amyotrophic Lateral Sclerosis, Biochimica et Biophysica Acta, 1832: 312-322, 2013.

Mehdi Ghasemi et al., The NMDA Receptor Complex as a Therapeutic Target in Epilepsy: a Review, Epilepsy & Behavior, 22: 617-640, 2011.

Seven E. Tomek et al., NMDA Receptor Modulators in the Treatment of Drug Addiction, Pharmaceuticals (Basel), 6: 251-268, 2013.

Chen, Jiali et al., Implication of Genes for the N-Methyl-D-Aspartate (NMDA) Receptor in Substance Addictions, Molecular Neurobiology, 2018, 12 pages.

Anthony M. Bolger et al., Trimmomatic: a Flexible Trimmer for Illumina Sequence Data, Bioinformatics, 1-7, 2014.

Hyun-Hwan Jeong et al., An Ultra-fast and Scalable Quantification Pipeline for Transposable Elements from Next Generation Sequencing Data, Pacific Symposium on Biocomputing, 168-179, 2018.

Liao, Yang et al., FeatureCounts: An Efficient General Purpose Program for Assigning Sequence Reads to Genomic Features, Bioinformatics, 1-8, 2013.

Joel Rozowsky et al., except: A Comprehensive Analytic Platform for Extracellular RNA Profiling, Cell, 8: 1-6, 2019.

RR Core Team, R: A language and environment for statistical computing, 2013, 12 pages.

Douglas Bates et al., Fitting Linear Mixed-Effects Models Using lme4, Journal of Statistical Software, 1-51, 2015.

* cited by examiner

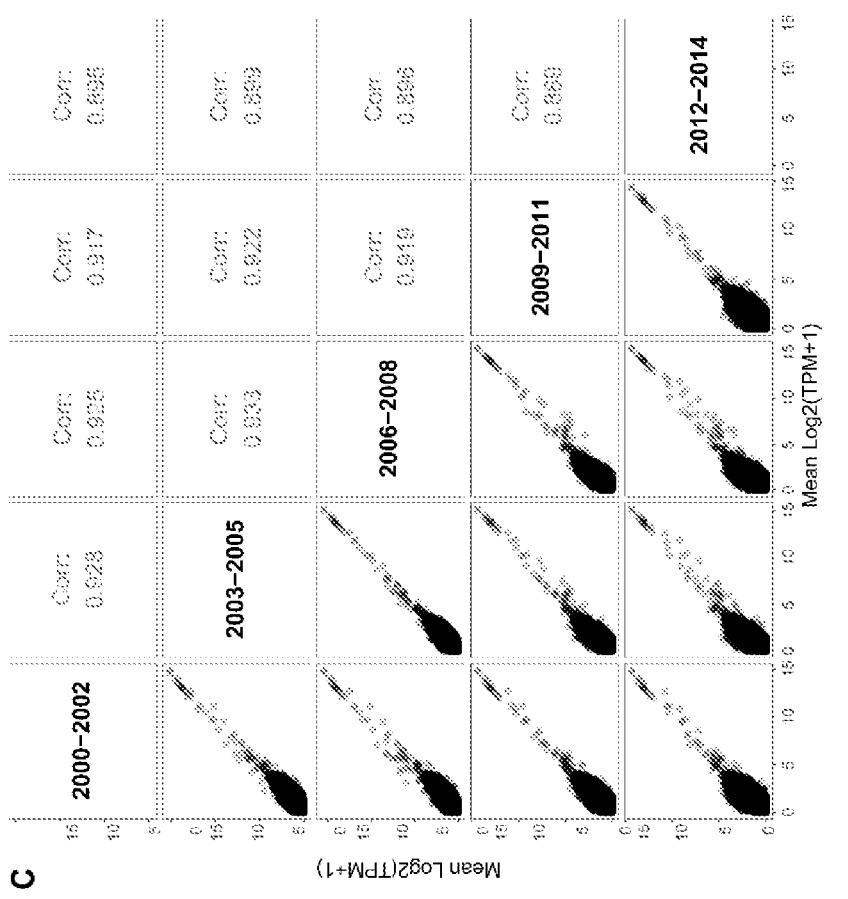
FIG. 2C
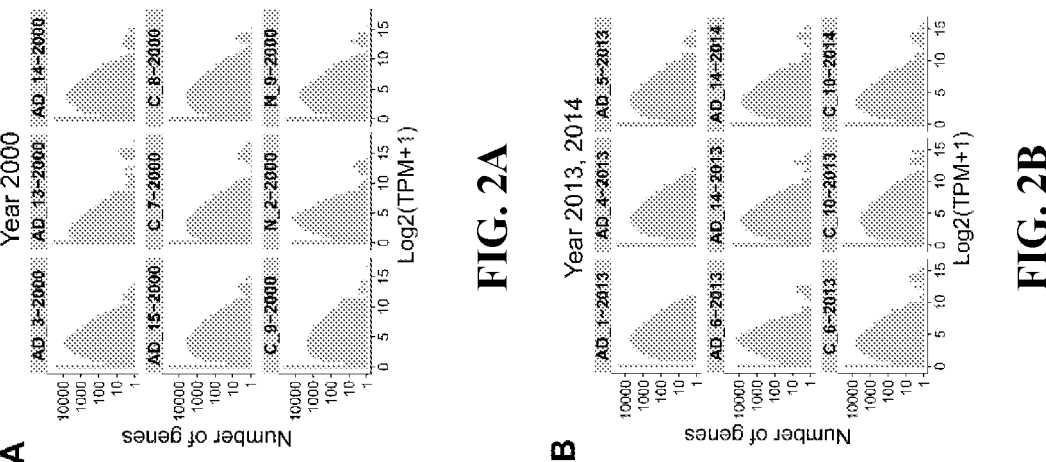
FIG. 2A
FIG. 2B

METHODS AND MATERIALS FOR DIAGNOSIS AND TREATMENT OF NEURONAL DISORDER

1. CROSS-REFERENCE TO RELATED APPLICATION

This application is a U.S. National Stage Application under 35 U.S.C. § 371 of International Patent Application No. PCT/US2021/019859, filed Feb. 26, 2021, which claims the benefit of U.S. Provisional Application No. 62/983,569 filed Feb. 28, 2020, the content of each of which is incorporated by reference in its entirety.

2. FIELD

Provided herein are methods of managing, preventing, or treating a neuronal disorder in a subject, such as Alzheimer's disease, comprising monitoring the expression level of phosphoglycerate dehydrogenase (PHGDH) in the subject over an observation period of time, and administering to the subject an effective amount of a therapy for managing, preventing or treating the neuronal disorder.

3. BACKGROUND

Alzheimer's disease (AD) is a progressive neurodegenerative disorder and the leading cause of dementia in the elderly. Increasing longevity in the past century has contributed to an exponential rise in AD. It is estimated more than 5 million people in the United States (US) currently suffer from AD. There is a need for new methods to manage, prevent, or treat AD and other neuronal disorders.

4. SUMMARY

In one aspect, provided herein are methods of managing, preventing, or treating a disorder, for example, a neuronal disorder associated with neuro-excitotoxicity, in a subject. In certain embodiments, the methods comprise (a) monitoring the expression level of phosphoglycerate dehydrogenase (PHGDH) in the subject over an observation period of time; and (b) administering to the subject an effective amount of a therapy for managing, preventing or treating the neuronal disorder, if the expression level of PHGDH is substantially increased during the observation period.

In another aspect, provided herein are methods of managing or treating a neuronal disorder associated with neuro-excitotoxicity in a subject who is under an ongoing first therapy for the neuronal disorder. In certain embodiments, the methods comprise comprising (a) monitoring the expression level of phosphoglycerate dehydrogenase (PHGDH) in the subject over an observation period of time; and (b) administering a second therapy to the subject, if the expression level of PHGDH is substantially increased during the observation period. In certain embodiments, the first therapy and second therapy are different.

In yet another aspect, provided herein are methods of diagnosing a neuronal disorder associated with neuro-excitotoxicity in a subject, comprising (a) monitoring the expression level of phosphoglycerate dehydrogenase (PHGDH) in the subject over an observation period of time; and (b) classifying the subject as having the neuronal disorder or at a high risk of developing the neuronal disorder, if the expression level of PHGDH is substantially increased during the observation period; or (c) classifying the subject as having a low risk of developing the neuronal disorder, if the expression level of PHGDH is substantially increased during the observation period.

In certain embodiments of the methods described herein, the neuronal disorder is Alzheimer's disease, schizophrenia, amyotrophic lateral sclerosis (ALS), epilepsy, or drug addiction. In certain embodiments of the methods described herein, the neuronal disorder is Alzheimer's disease.

5. BRIEF DESCRIPTION OF THE DRAWINGS

FIG. 1 shows a summary of this 15-year follow-up study. Plasma collection time (dot) is denoted for each donor (line) from Year 2000 to 2015 (x axis). The 3 groups of participants are colored in blue (top group), red (middle group), and green (bottom group). Cross: the time of change in clinical diagnosis. The individual was diagnosed with normal cognition before this time and impaired cognition on this time.

FIGS. 2A to 2C shows comparison of exRNA levels across the years. FIG. 2A shows distributions of measured exRNAs in year 2000; FIG. 2B shows distributions of measured exRNAs in year 2013-2014; FIG. 2C are scatterplots (lower left) and correlations (upper right) between every two pair of time intervals, 2000-2002, 2003-2005, 2006-2008, 2009-2011, and 2012-2014.

Figures 3A, 3B:
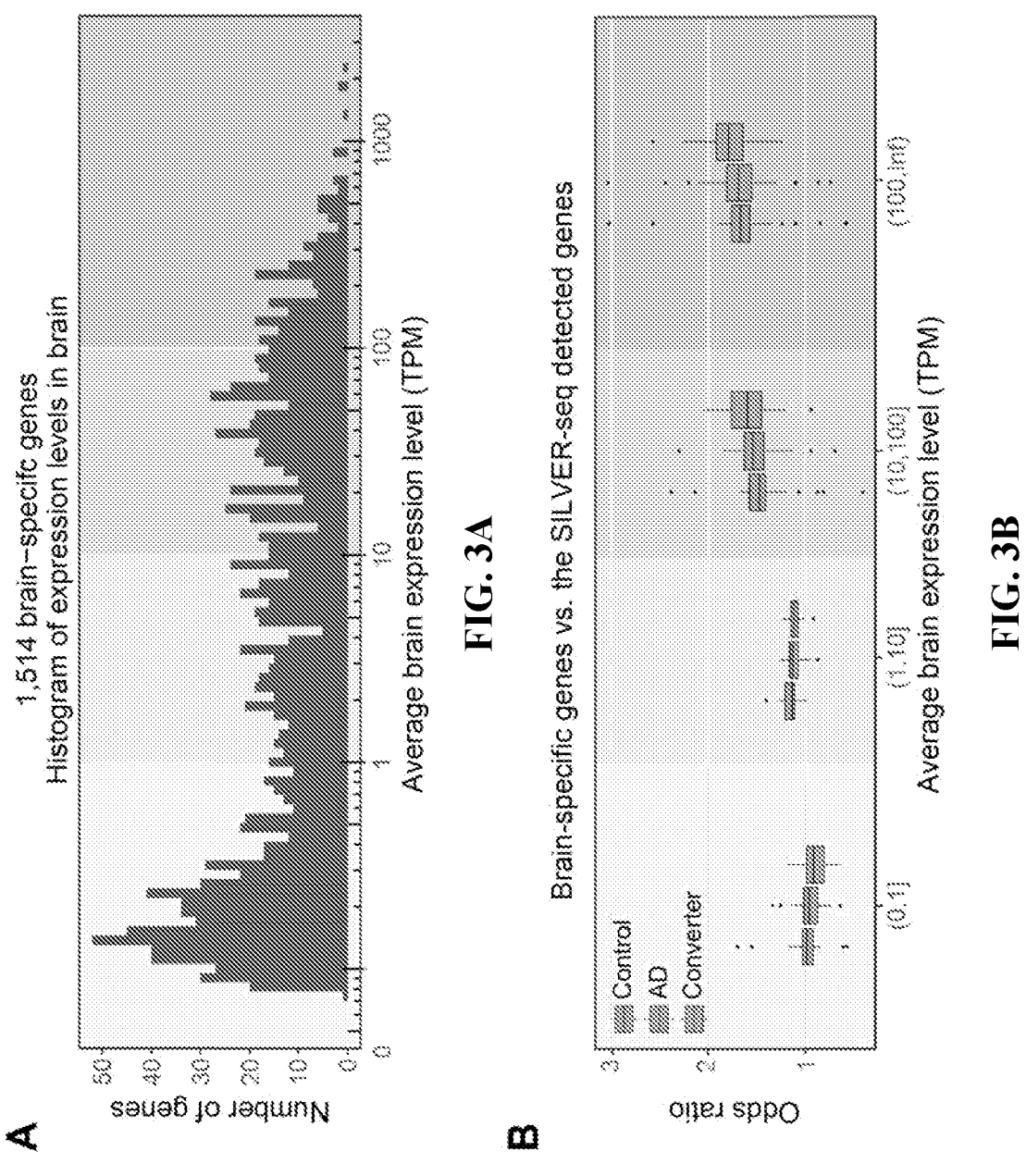

FIGS. 3A and 3B shows association of brain-specific genes and the SILVER-seq detected genes in plasma. FIG. 3A is a histogram of the brain expression levels (the average TPM of GTEx assayed brain regions) of the brain-specific genes (x axis). These brain-specific genes are categorized into 4 groups of increasing expression levels in brain (vertical shades). FIG. 3B shows distributions of the odds ratios between the brain-specific genes in each expression group (TPM=(0,1], (1,10], (10,100], (100, infinity), x axis) and those genes detected in each plasma sample (SILVER-seq's TPM>5). The odds ratio derived from a plasma sample corresponds to a data point in each expression group (vertical shade). Each boxplot summaries the ratios derived from the AD (middle), control (left), and converter (right) plasma samples.

Figures 4A, 4B, 4C, 4D, 4E:
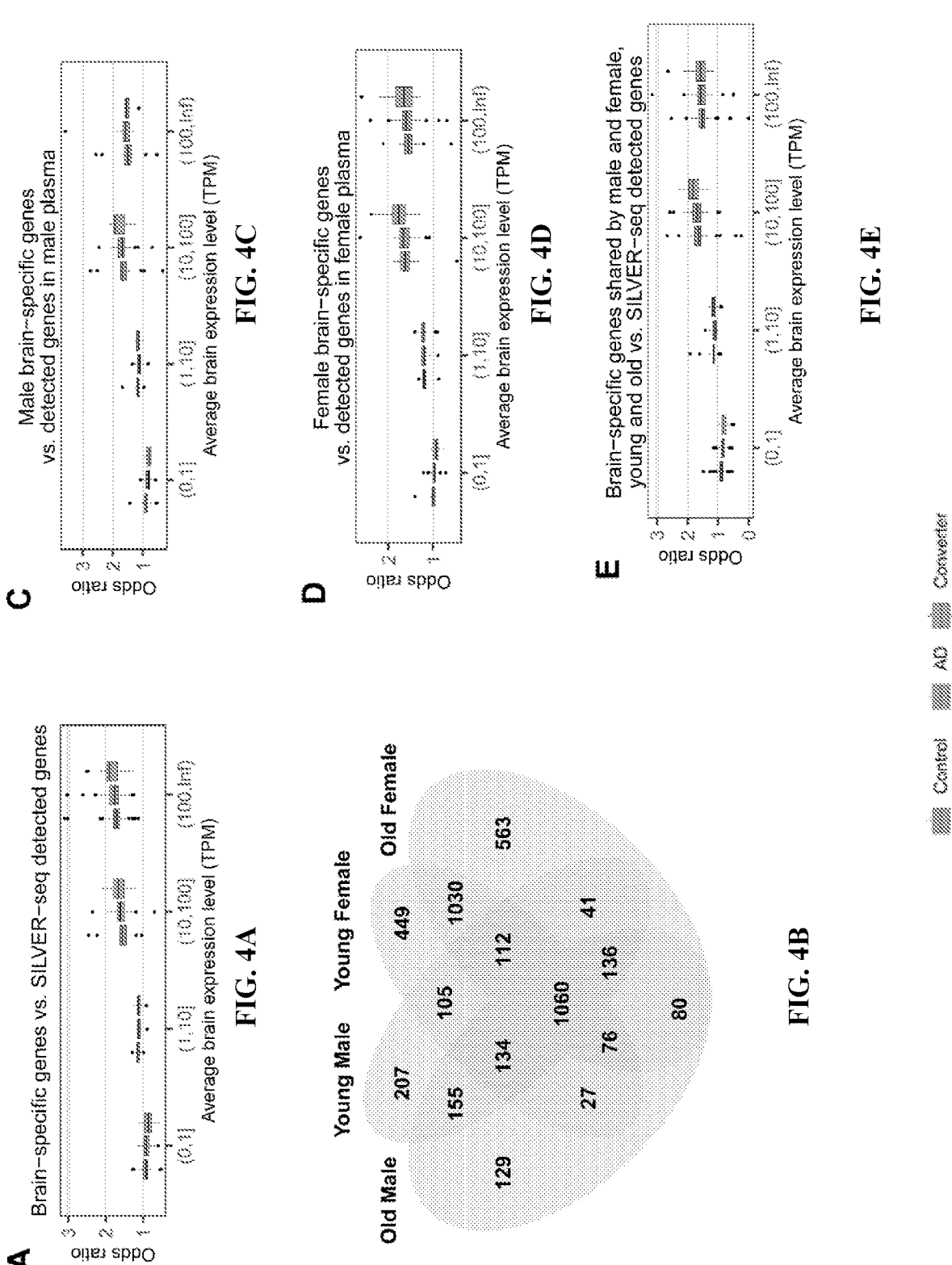
Figures 4F, 4G:
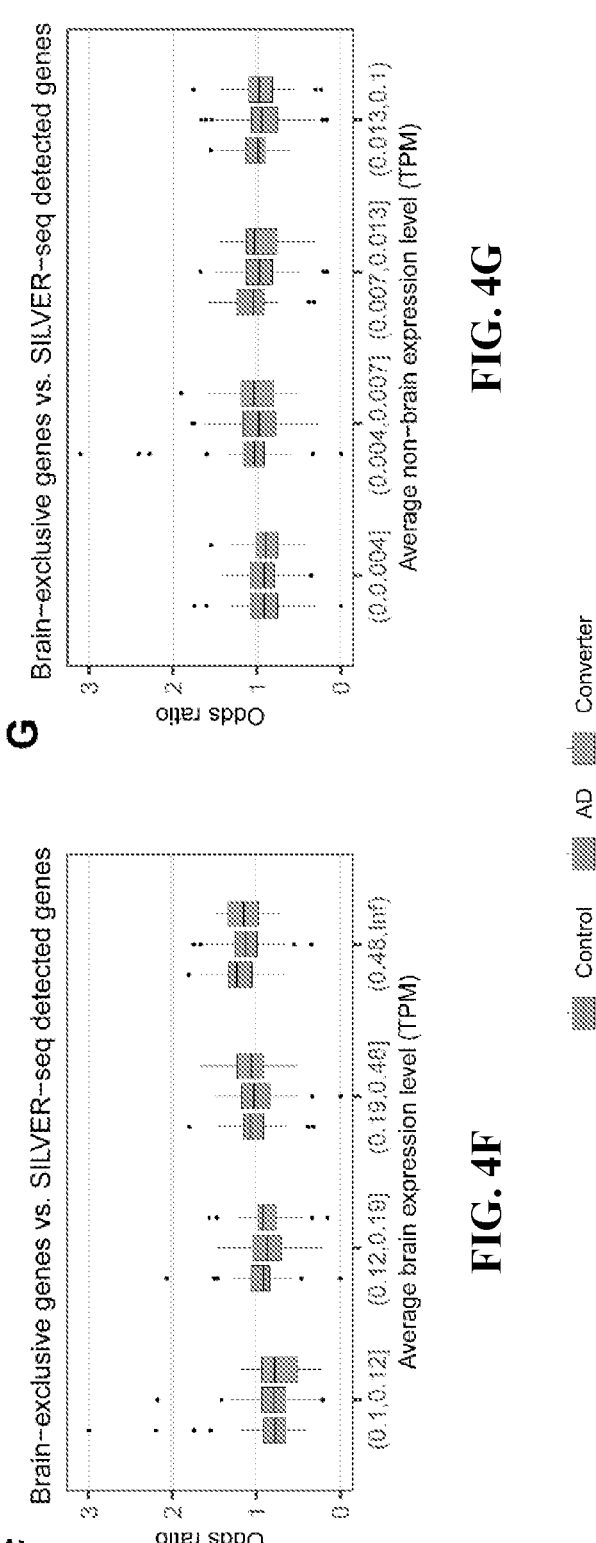

FIGS. 4A to 4G show robustness analysis of the association of brain-specific genes and the SILVER-seq detected genes in plasma. FIG. 4A shows distributions of the odds ratios between the brain-specific genes in each expression group (TPM=(0,1], (1,10], (10,100], (100, infinity), x axis) and those genes detected in each plasma sample (SILVER-seq's TPM>3). FIG. 4B shows Venn diagram of brain-specific genes from young female, old female, young male, and old male samples of GTEx V8 data. FIG. 4C, FIG. 4D and FIG. 4E show Distributions of the odds ratios between the male (C), female (D), and shared (E) brain-specific genes in each expression group (x axis) and those genes detected in the male, female, and all plasma samples (SILVER-seq's TPM>5). FIG. 4F shows distributions of the odds ratios between the brain-exclusive genes in each brain expression quartile and those genes detected in each plasma sample (SILVER-seq's TPM>5). FIG. 4G shows distributions of the odds ratios between the brain-exclusive genes in each expression quartile of non-brain tissues and those genes detected in each plasma sample (SILVER-seq's TPM>5). Each boxplot summaries the ratio ratios derived from the AD (middle), control (left), and converter (right) plasma samples.

Figures 5A, 5B:
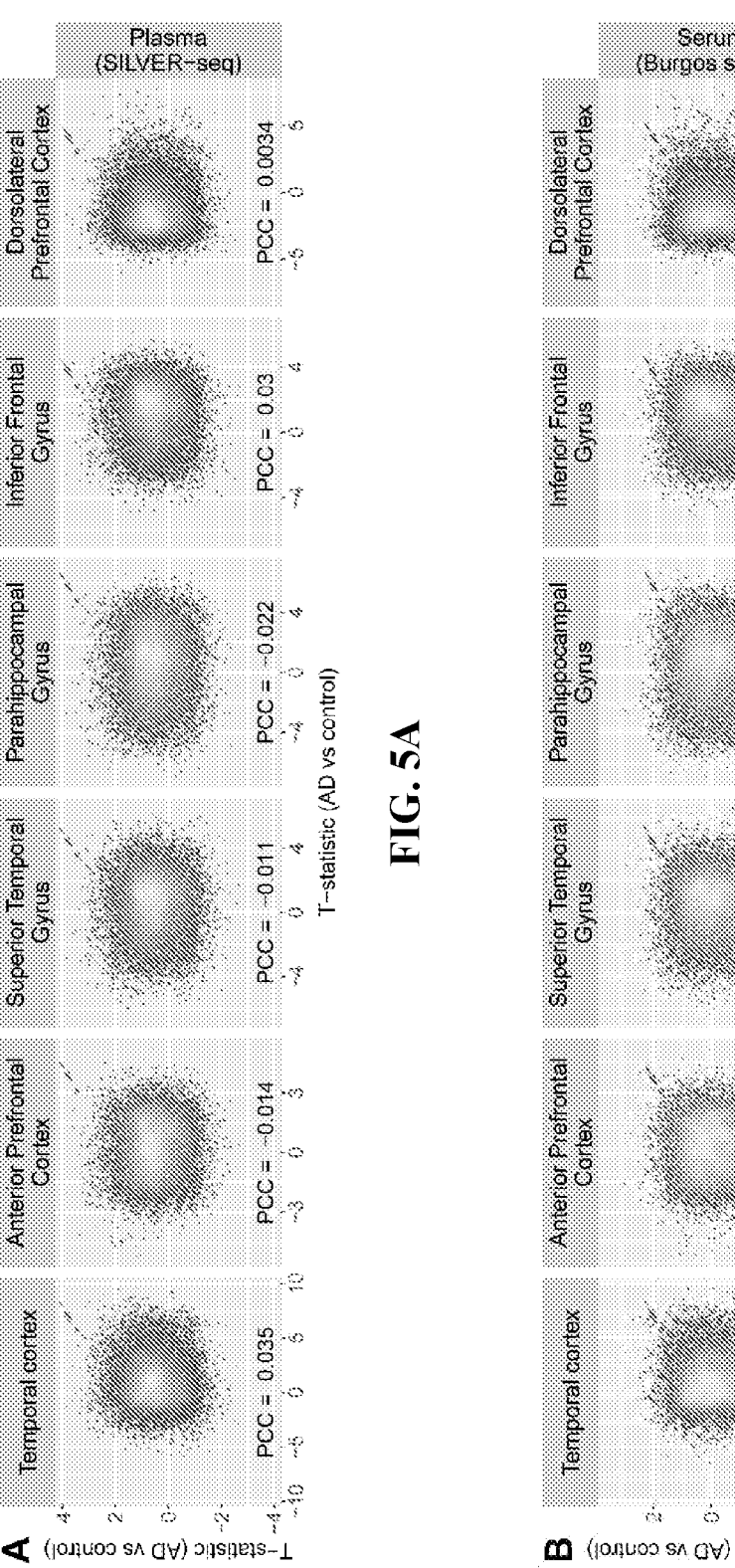

FIGS. 5A and 5B show comparison of brain gene expression changes to plasma (A) and serum (B) exRNA changes. FIG. 5A are scatterplots of the T statistic (AD vs control) of each RNA (dot) in plasma (y axis) and in each brain region (x axis). FIG. 5B are scatterplots of the T statistic (AD vs control) of each RNA (dot) in serum (y axis) and in each brain region (x axis). Yellow-to-blue gradient reflects the decreasing data point densities. Arrow: PHGDH.

Figure 6C:
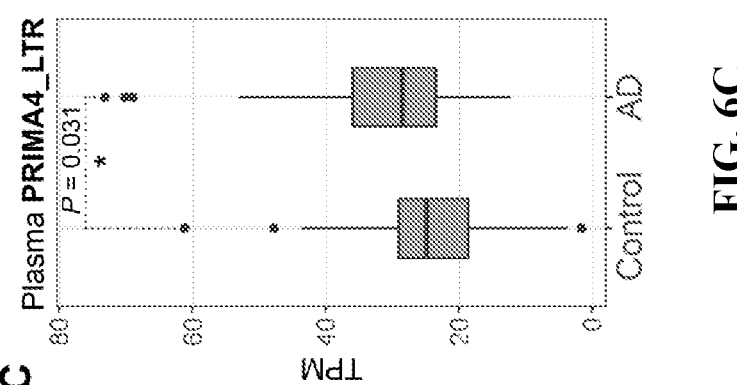
Figure 6B:
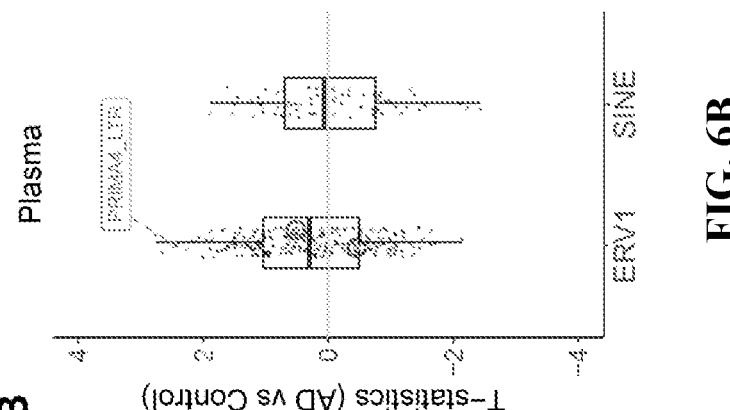
Figure 6A:
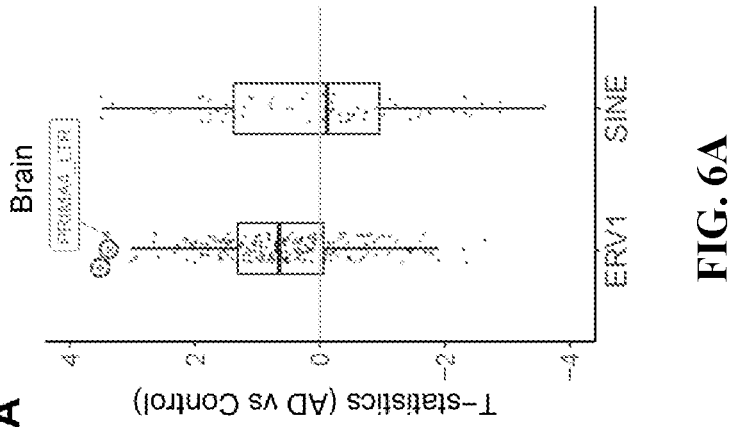

FIGS. 6A to 6C show consistent AD-associated increase of ERV1 transposon transcripts in brain and plasma. FIG. 6A shows the T statistics (y axis) derived by Guo et al. from comparing AD brains to control brains for every transposon (dot) in the ERV1 and the SINE clades (columns). T statistic >0 corresponds to AD-associated increase in brain. The 3 ERV1 transposons with the largest increments are shown in dots circled by a dashed line or a solid line, or marked as "PRIMA4_LTR." FIG. 6B shows the T statistics (y axis) derived from a comparison of AD plasma and control plasma for every transposon (dot) in the ERV1 and the SINE clades (columns). T statistic >0 corresponds to AD-associated increase in plasma. The 3 colored dots correspond to the 3 colored ERV1 transposons in panel A. PRIMA4_LTR (red dot) is among the few transposons with strongest increases in plasma. FIG. 6C shows comparison of plasma PRIMA4_LTR levels in control (left) and AD (right). The reported p-value is based on an ANOVA test controlling for sex and APOE status.

Figures 7A, 7B:
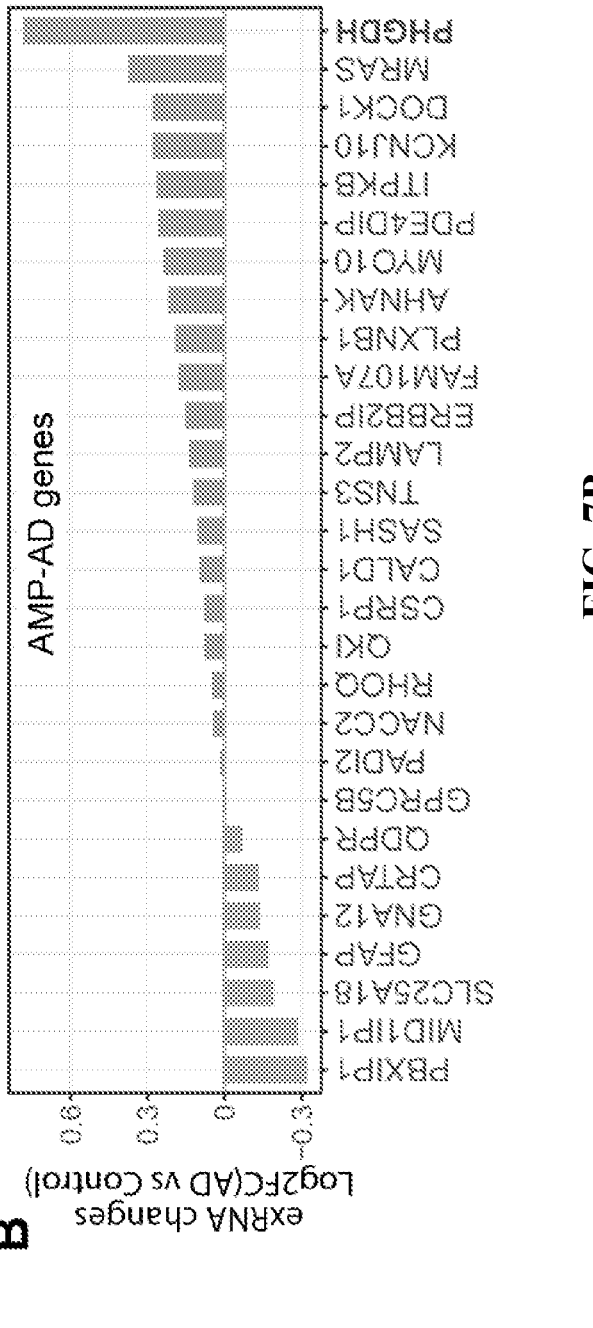
Figures 7C, 7D:
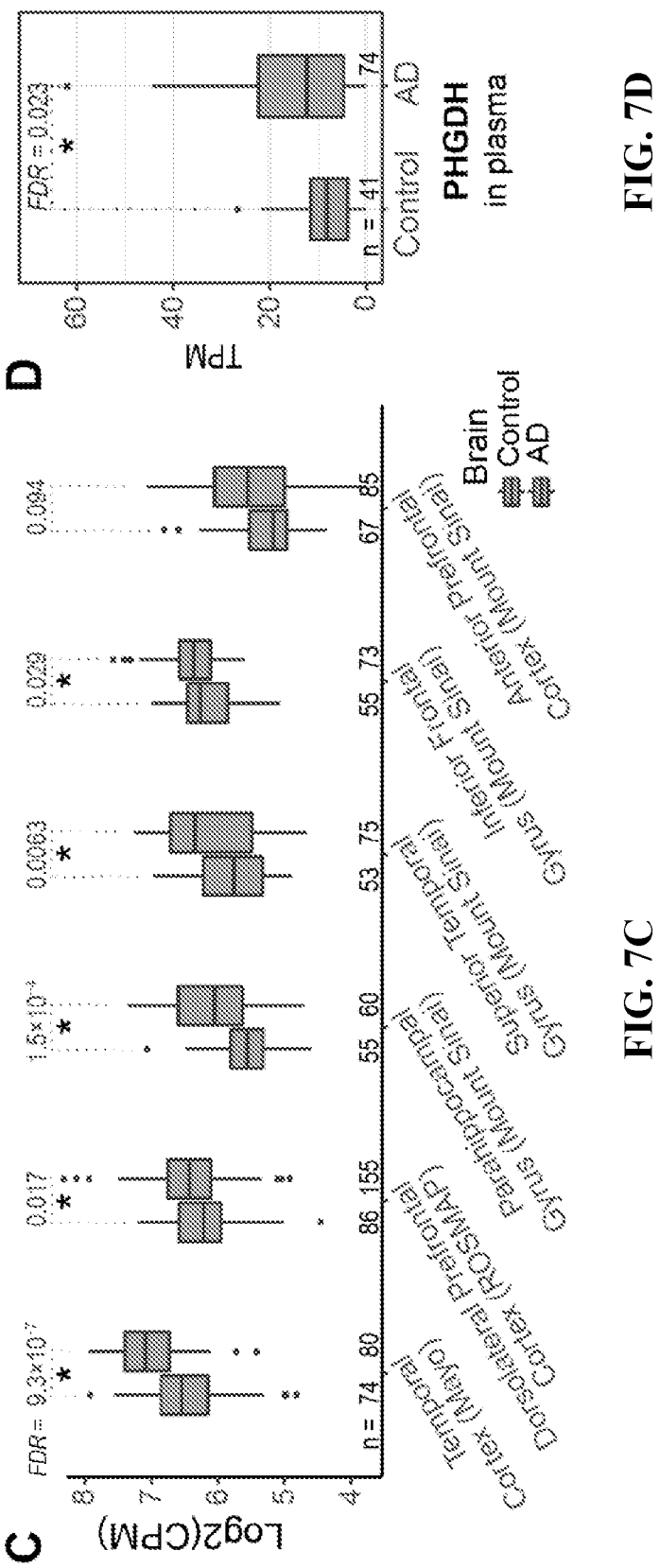
Figures 7E, 7F, 7G:
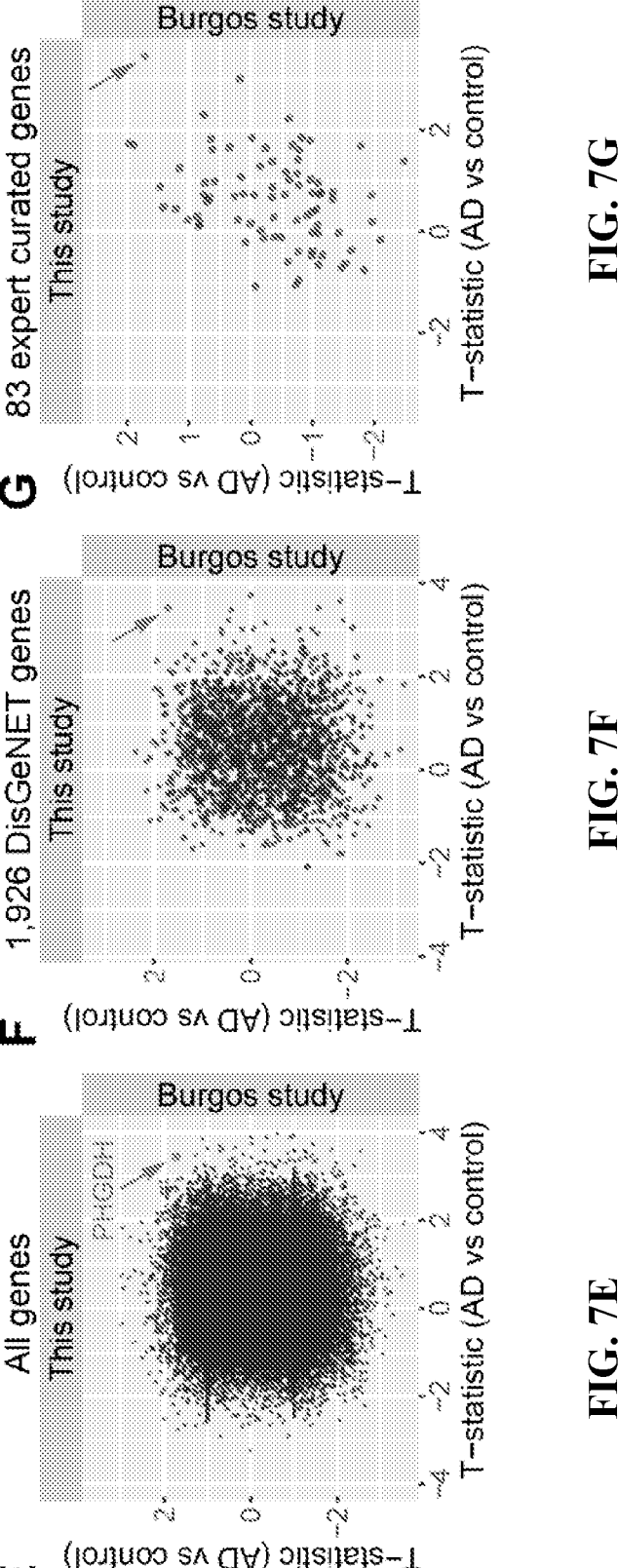
Figures 7H, 7I, 7J, 7K, 7L:
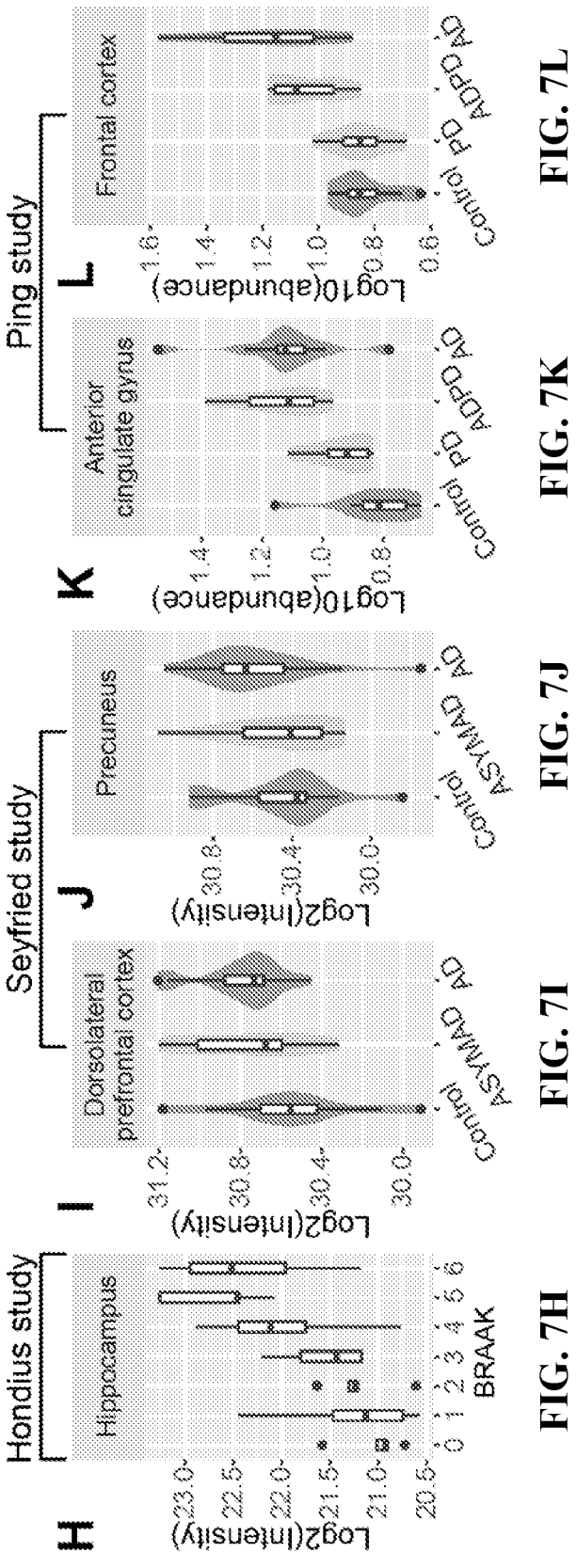

FIGS. 7A to 7L show changes of plasma exRNA levels of the AMP-AD genes. FIG. 7A shows distributions oft statistics (AD plasma vs. control plasma) for all genes, lipid metabolic process genes, and AMP-AD genes (columns). FIG. 7B shows log fold change for each AMP-AD-gene (column) (B). FIG. 7C shows PHGDH expression levels in each brain region (x axis) in control (left) and AD (right). The cohort name of each study is given in brackets. FIG. 7D shows plasma PHGDH levels in control (left) and AD (right). FDR is based on ANOVA tests controlling for sex and APOE status. FIG. 7E, FIG. 7F and FIG. 7G show comparison of exRNA changes between two cohorts. The AD-versus-control changes for each exRNA (dot) is represented by a T statistic from our cohort (x axis) and from the Burgos cohort (y axis). The correlations increased from all genes (E), the 1,926 database recorded genes and PHGDH (arrow pointed dot) (F), and the 83 expert curated genes and PHGDH (arrow pointed dot) (G). FIGS. 7H to 7L show changes of PHGDH protein levels in brain. Particularly FIG. 711 shows Distributions of hippocampal PHGDH protein levels (box plots) in each Braak stage (x axis). Braak stage=0: no AD pathology. FIG. 7I and FIG. 7J show distributions dorsolateral prefrontal cortex (I) and precuneus (J) PHGDH protein levels (violin plots) in controls (left), asymptomatic AD (middle), and AD (right). FIG. 7K and FIG. 7L show distributions of anterior cingulate gyms (K) and frontal cortex (L) PHGDH protein levels (violin plots) in controls (left), Parkinson disease (PD, middle left), AD and PD co-morbid patients (ADPD, middle right), and AD (right).

Figures 8A, 8B, 8C, 8D:
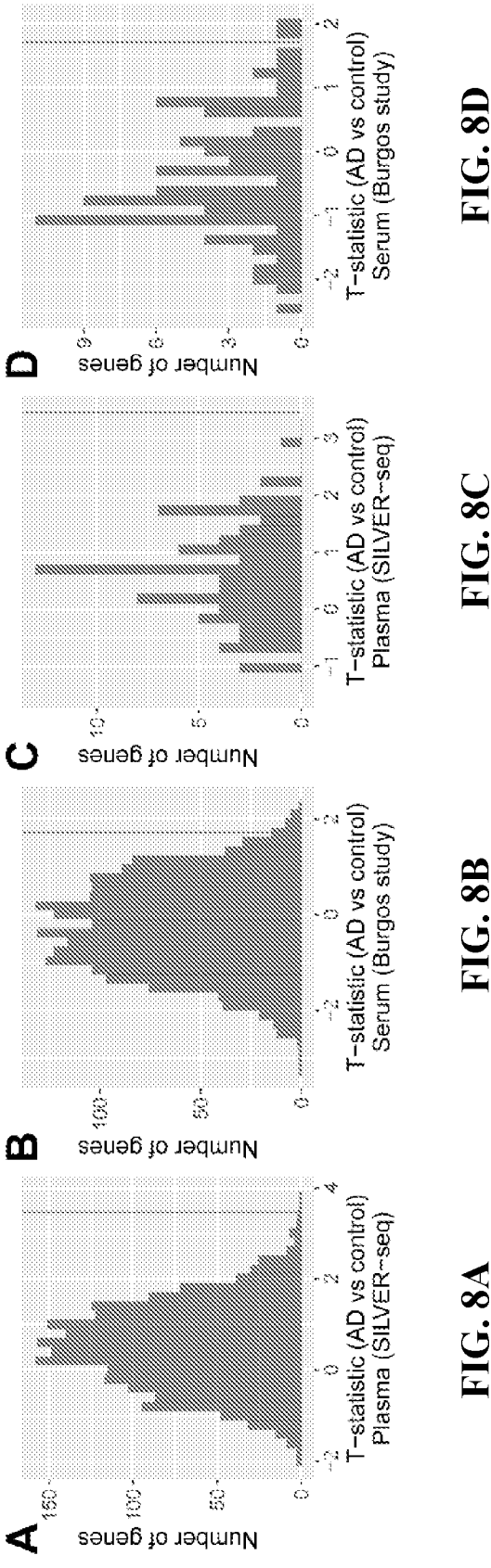

FIGS. 8A to 8D show AD-versus-control exRNA changes in the two cohorts. FIG. 8A and FIG. 8B are histograms of the 1,981 T statistics of the 1,981 DisGeNET documented AD-associated genes in plasma (A) and serum samples (B). FIG. 8C and FIG. 8D are histograms of the 84 t statistics of the 84 expert curated AD-associated genes in plasma (C) and serum samples (D). Vertical line: PHGDH's t statistic.

Figure 9A:
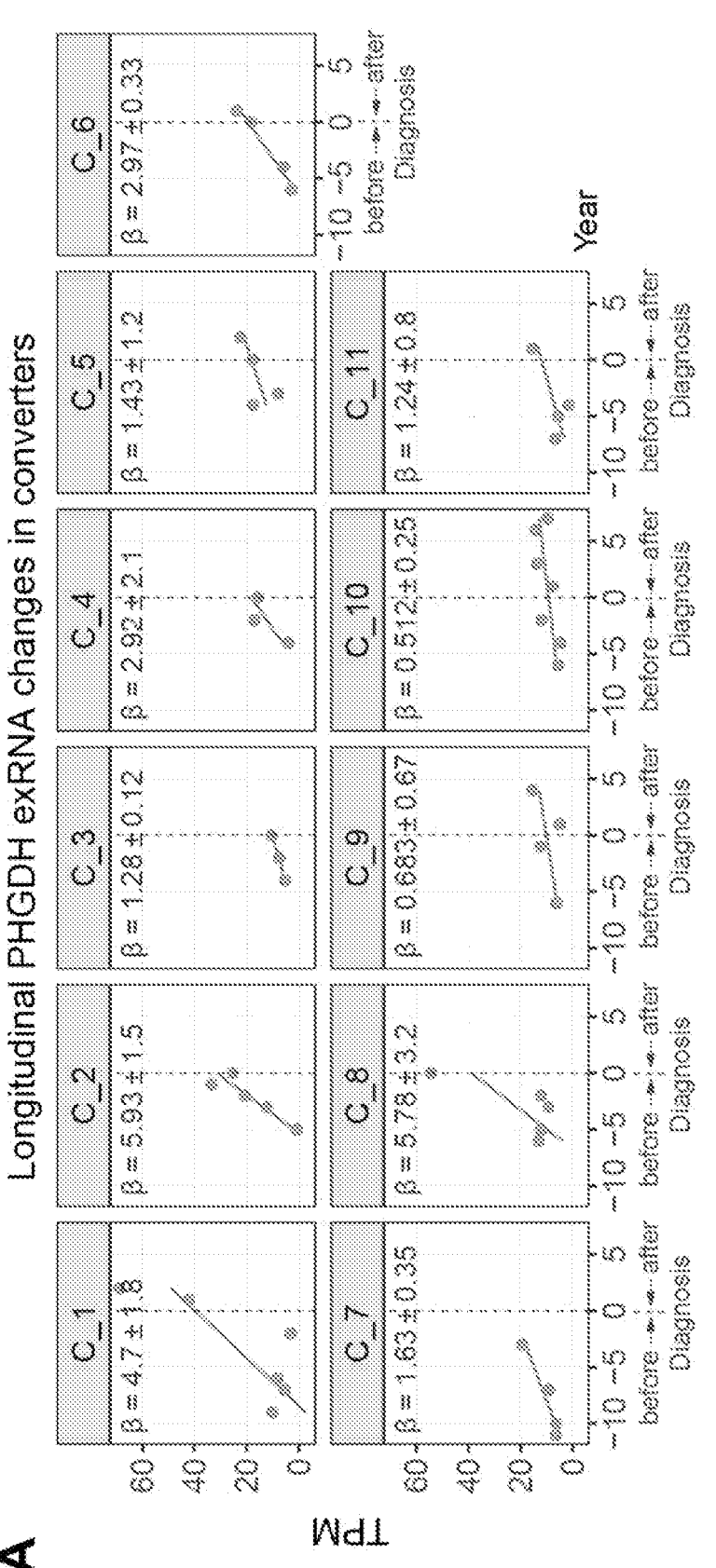
Figures 9B, 9C:
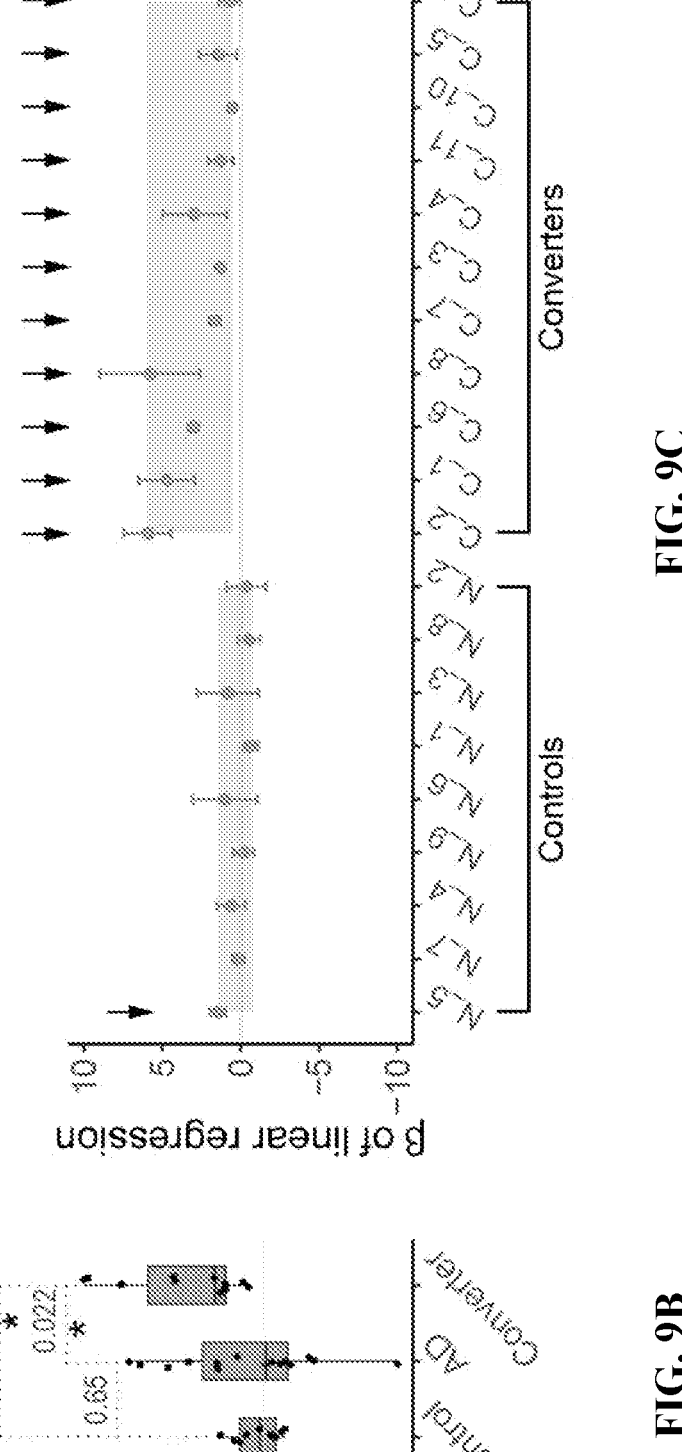

FIGS. 9A to 9C show longitudinal changes of plasma PHGDH. FIG. 9A shows PHGDH exRNA levels (y axis) across time (x axis) in each converter (C1-C11). The time of clinical diagnosis of cognitive impairment is set as Year 0. Negative and positive years correspond to the years before and after diagnosis. The regression coefficient (β) from a linear regression (line) summarizes the overall change over time for each converter. A positive β corresponds to exRNA increase over time. FIG. 9B shows the β (y axis) of longitudinal changes of plasma PHGDH for every participant (dot) in controls (left), AD (middle), and converters (right). FIG. 9C shows β (dot) and its standard deviation (whisker) for controls (left group) and converters (right group). Arrows: participants with the lower whisker above 0 (β−standard deviation of β>0).

6. DETAILED DESCRIPTION

Before the present disclosure is further described, it is to be understood that the disclosure is not limited to the particular embodiments set forth herein, and it is also to be understood that the terminology used herein is for the purpose of describing particular embodiments only, and is not intended to be limiting.

6.1.1 Terminology

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications, and other publications are incorporated by reference in their entirety. In the event that any description of terms set forth conflicts with any document incorporated herein by reference, the description of term set forth below shall control.

The term "extracellular RNA" or "exRNA" encompasses all RNA molecules that are present outside the cell in which they were transcribed in a subject.

As used herein, the Phosphoglycerate Dehydrogenase (PHGDH) gene encodes the enzyme which is involved in the early steps of L-serine synthesis in animal cells. As used herein, the term "Phosphoglycerate Dehydrogenase," "D-3-phosphoglycerate dehydrogenase," "3-PGDH," or "PHDGH," encompasses a gene, from any vertebrate source, including mammals such as primates (e.g., humans and cynomolgus monkeys (cynomolgus)), chicken, lizard, zebrafish, and rodents (e.g., mice and rats), unless otherwise indicated. As used herein, the term "Phosphoglycerate Dehydrogenase," "D-3-phosphoglycerate dehydrogenase," "3-PGDH," or "PHDGH," also encompasses a gene product. In other embodiments, the gene product is an RNA. In other embodiments the gene product is a polypeptide ("polypeptide" and "protein" are used interchangeably herein). In certain embodiments, the terms also include SNP variants thereof.

In some embodiments, the PHGDH has an amino acid sequence of: MAFANLRKVLISDSLDPCCRKILQDG-GLQVVEKQNLSKEELIAELQDCEGLIVRSATKVT AD-VINAAEKLQVVGRAGTGVDNVDLEAATRKGILVM-NTPNGNSLSAAELTCGMIMCL ARQIPQATASMKDG-KWERKKFMGTELNGKTLGILGLGRIGREVATRMQ-SFGMKTIGYD PIISPEVSASFGVQQLPLEEIWPLCD-FITVHTPLLPSTTGLLNDNTFAQCKKGVRVVNCAR GGIVDEGALLRALQSGQCAGAALDVFTEEPPRDR-ALVDHENVISCPHLGASTKEAQSRC GEEIAVQFVD-MVKGKSLTGVVNAQALTSAFSPHTKPWIGLAEAL-GTLMRAWAGSPKGT IQVITQGTSLKNAGNCLSPAV-IVGLLKEASKQADVNLVNAKLLVKEAGLNVTTSH-SPAA PGEQGFGECLLAVALAGAPYQAVGLVQGTTP-VLQGLNGAVFRPEVPLRRDLPLLLFRTQ TSD- PAMLPTMIGLLAEAGVRLLSYQTSLVSDG- ETWH-VMGISSLLPSLEAWKQHVTEAFQ FHF (SEQ ID NO.: 1) GenBank™ accession number NG 009188 provides an exemplary human PHGDH nucleic acid sequence.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a disease, disorder, or condition, including, for example, Alzhemier's disease. In some embodiments, the effective amount is a therapeutically effective amount or a prophylactically effective amount.

The term "therapeutically effective amount" as used herein refers to the amount of an agent (e.g., an antibody provided herein or any other agent described herein) that is sufficient to reduce and/or ameliorate the severity and/or duration of a given disease, disorder, or condition, and/or a symptom related thereto (e.g., Alzheimer's disease). A "therapeutically effective amount" of a substance/molecule/agent of the present disclosure may vary according to factors such as the disease state, age, sex, and weight of the individual, and the ability of the substance/molecule/agent to elicit a desired response in the individual. A therapeutically effective amount encompasses an amount in which any toxic or detrimental effects of the substance/molecule/agent are outweighed by the therapeutically beneficial effects. In certain embodiments, the term "therapeutically effective amount" refers to an amount of an antibody or other agent (e.g., drug) effective to "treat" a disease, disorder, or condition, in a subject or mammal.

A "prophylactically effective amount" is an amount of a pharmaceutical composition that, when administered to a subject, will have the intended prophylactic effect, e.g., preventing, delaying, or reducing the likelihood of the onset (or reoccurrence) of a disease, disorder, condition, or associated symptom(s) (e.g., Alzheimer's disease). Typically, but not necessarily, since a prophylactic dose is used in subjects prior to or at an earlier stage of a disease, disorder, or condition, a prophylactically effective amount may be less than a therapeutically effective amount. The full therapeutic or prophylactic effect does not necessarily occur by administration of one dose, and may occur only after administration of a series of doses. Thus, a therapeutically or prophylactically effective amount may be administered in one or more administrations.

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule.

"Polynucleotide" or "nucleic acid," as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides.

Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

The term "encoding nucleic acid" or grammatical equivalents thereof as it is used in reference to nucleic acid molecule refers to a nucleic acid molecule in its native state or when manipulated by methods well known to those skilled in the art that can be transcribed to produce mRNA, which is then translated into a polypeptide and/or a fragment thereof. The antisense strand is the complement of such a nucleic acid molecule, and the encoding sequence can be deduced therefrom.

The terms "prevent," "preventing," and "prevention" refer to reducing the likelihood of the onset (or recurrence) of a disease, disorder, condition, or associated symptom(s) (e.g., Alzheimer's disease).

The terms "subject" and "patient" may be used interchangeably. As used herein, in certain embodiments, a subject is a mammal, such as a non-primate (e.g., cow, pig, horse, cat, dog, rat, etc.) or a primate (e.g., monkey and human). In specific embodiments, the subject is a human. In one embodiment, the subject is a mammal (e.g., a human) having a neuronal disorder or condition. In another embodiment, the subject is a mammal (e.g., a human) at risk of developing a neuronal disease, disorder, or condition.

"Substantially all" refers to at least about 60%, at least about 65%, at least about 70%, at least about 75%, at least about 80%, at least about 85%, at least about 90%, at least about 95%, at least about 98%, at least about 99%, or about 100%.

The term "therapeutic agent" refers to any agent that can be used in treating, preventing, or alleviating a disease, disorder, or condition, including in the treatment, prevention, or alleviation of one or more symptoms of a neuronal disorder, disorder, or condition and/or a symptom related thereto. In certain embodiments, a therapeutic agent refers to an NMDA receptor antagonist as described herein. In certain embodiments, the NMDA receptor antagonist are selected from competitive antagonists such as but not limited to AP5 (APV, R-2-amino phosphonopentanoate), AP7 (2-amino-7-phosphonoheptanoic acid), CPPene (3-[(R)-2-carboxypiperazin-4-yl]-prop-2-enyl-1-phosphonic acid), Selfotel, Aspartame, uncompetitive channel blockers, such as but not limited to 3-MeO-PCP, 8A-PDHQ, Amantadine, Atomoxetine, AZD6765, Agmatine, Chloroform, Delucemine, Dextrallorphan, Dextromethorphan, Dextrorphan, Diphenidine, Dizocilpine (MK-801), Ethanol, Eticyclidine, Gacyclidine, Ketamine, Magnesium, Memantine, Methoxetamine, Minocycline, Nitromemantine, Nitrous oxide, PD-137889, Phencyclidine, Rolicyclidine, Tenocyclidine, Methoxydine, Tiletamine, Neramexane, Eliprodil, Etoxadrol, Dexoxadrol, WMS-2539, NEFA, Remacemide; noncompetitive antagonists such as but not limited to Aptiganel (Cerestat, CNS-1102), HU-211, Huperzine, Ibogaine, Remacemide, Rhynchophylline, Gabapentin; and Glycine antagonists, such as but not limited to Rapastinel (GLYX-13), NRX-1074, 7-Chlorokynurenic acid, 4-Chlorokynurenine (AV-101), 5,7-Dichlorokynurenic acid, Kynurenic acid, TK-40, 1-Aminocyclopropanecarboxylic acid (ACPC), L-Phenylalanine, Xenon.

The term "therapy" refers to any protocol, method, and/or agent that can be used in the prevention, management, treatment, and/or amelioration of a neuronal disorder, or condition. In certain embodiments, the terms "therapies" and "therapy" refer to a biological therapy, supportive therapy, and/or other therapies useful in the prevention, management, treatment, and/or amelioration of a neuronal disorder, disorder, or condition, known to one of skill in the art such as medical personnel.

The terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., prophylactic or therapeutic agents to "manage" a neuronal disorder, one or more symptoms thereof, so as to prevent the progression or worsening of the disease.

The terms "about" and "approximately" mean within 20%, within 15%, within 10%, within 9%, within 8%, within 7%, within 6%, within 5%, within 4%, within 3%, within 2%, within 1%, or less of a given value or range.

"Administer" or "administration" refers to the act of injecting or otherwise physically delivering a substance as it exists outside the body into a patient, such as by mucosal, intradermal, intravenous, intramuscular delivery, and/or any other method of physical delivery described herein or known in the art. When a disease, disorder, condition, or a symptom thereof, is being treated, administration of the substance typically occurs after the onset of the disease, disorder, condition, or symptoms thereof. When a disease, disorder, condition, or symptoms thereof, are being prevented, administration of the substance typically occurs before the onset of the disease, disorder, condition, or symptoms thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a," "and," and "the" include plural referents unless the context clearly indicates otherwise. Thus, for example, reference to "a peptide sequence" includes a plurality of such sequences and so forth.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc. In a further example, reference to a range of 25-250, 250-500, 500-1,000, 1,000-2,500, 2,500-5,000, 5,000-25,000, 25,000-50,000 includes any numerical value or range within or encompassing such values, e.g., 25, 26, 27, 28, 29 . . . 250, 251, 252, 253, 254 . . . 500, 501, 502, 503, 504 . . . , etc.

As also used herein a series of ranges are disclosed throughout this document. The use of a series of ranges include combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth. The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

6.1.2 Methods

In one aspect, provided herein is a method of managing, preventing, or treating a disorder, for example, a neuronal disorder associated with neuro-excitotoxicity, in a subject. In certain embodiments, the method comprises (a) monitoring the expression level of phosphoglycerate dehydrogenase (PHGDH) in the subject over an observation period of time; and (b) administering to the subject an effective amount of a therapy for managing, preventing or treating the neuronal disorder, if the expression level of PHGDH is substantially increased during the observation period.

In some embodiments, the therapy comprises at least one NMDA receptor antagonist. In some embodiments, the NMDA receptor antagonist is memantine. In some embodiments, the therapy comprises at least one agent inhibiting in vivo production of glycine and/or serine in the subject. In some embodiments, the agent inhibiting in vivo production of glycine and/or serine is a PHGDH inhibitor. In some embodiments, the therapy comprises at least one agent inhibiting in vivo transportation of glycine and/or serine to excitatory synapses in the subject.

In some embodiments, the method further comprises (c) extending the observation period for an extended period, if the expression level of PHGDH is not substantially increased during the observation period. In some embodiments, the observation period is at least 1 month, 6 months, 12 months, 18 months, 2 years, or 5 years. In some embodiments, the observation period is at least 3 years. In some embodiments, the extended period is at least 1 month, 6 months, 12 months, 18 months, 2 years, or 5 years. In some embodiments, the methods comprise measuring the expression level about every 6 months or about every year during the extended period. In some embodiments, the subject is asymptomatic of the neuronal disorder at the beginning or during the observation period. In some embodiments, the subject is suspected of having, or at risk of developing, the neuronal disorder at the beginning or during the observation period. In some embodiments, the subject is considered an elderly individual in a country where the method is performed. In some embodiments, the subject is at least about 65 years old or at least about 70 years old. In some embodiments, the subject has a family history of the neuronal disorder.

In another aspect, provided herein is a method of managing or treating a neuronal disorder associated with neuro-excitotoxicity in a subject who is under an ongoing first therapy for the neuronal disorder. In certain embodiments, the methods comprise comprising (a) monitoring the expression level of phosphoglycerate dehydrogenase (PHGDH) in the subject over an observation period of time; and (b) administering a second therapy to the subject, if the expression level of PHGDH is substantially increased during the observation period. In certain embodiments, the first therapy and second therapy are different.

In some embodiments, the method further comprises (c) ceasing the ongoing first therapy, if the expression level of PHGDH is substantially increased during the observation period. In some embodiments, the method further comprises (c) ceasing the ongoing first therapy, if the expression level of PHGDH is not substantially increased during the observation period. In some embodiments, the method further comprises (c) ceasing the ongoing first therapy and administering a third therapy to the subject, if the expression level of PHGDH is not substantially increased during the observation period. In some embodiments, the first therapy does not comprise a NMDA receptor antagonist, and wherein the second therapy and/or third therapy comprises at least one NMDA receptor antagonist. In some embodiments, the first therapy comprise a NMDA inhibitor for threating a mild case of the neuronal disorder, and wherein the second therapy comprises a NMDA receptor antagonist for treating a severe case of the neuronal disorder. In some embodiments, the second therapy comprises memantine. In some embodiments, the first therapy comprises a NMDA receptor antagonist. In some embodiments, the first therapy comprises at least one NMDA receptor antagonist, and wherein the third therapy does not comprise any NMDA receptor antagonist. In some embodiments, the first therapy comprises a NMDA inhibitor for threating a severe case of the neuronal disorder, and wherein the second therapy comprises a NMDA receptor antagonist for treating a mild case of the neuronal disorder. In some embodiments, the second therapy comprises memantine. In some embodiments, the method further comprises extending the observation period for an extended period.

In yet another aspect, provided herein is a method of diagnosing a neuronal disorder associated with neuro-excitotoxicity in a subject, comprising (a) monitoring the expression level of phosphoglycerate dehydrogenase (PHGDH) in the subject over an observation period of time; and (b) classifying the subject as having the neuronal disorder or at a high risk of developing the neuronal disorder, if the expression level of PHGDH is substantially increased during the observation period; or (c) classifying the subject as having a low risk of developing the neuronal disorder, if the expression level of PHGDH is substantially increased during the observation period. In some embodiments, the risk is a risk of developing the neuronal disorder in less than about 5 years, less than about 2 years, or less than about 1 year. In some embodiments, the risk is a risk of having the onset of symptom for the neuronal disorder in less than about 5 years, less than about 2 years, or less than about 1 year.

In certain embodiments of the methods described herein, monitoring the expression level of PHGDH comprises providing a series of samples taken from the subject at sequential time points before or during the observation period. In some embodiments, at least one of the series of samples is a sample preserved from a time point before the observation period. In some embodiments, extending the observation period comprises taken at least one additional sample from the subject and measuring expression level of PHGDH using said sample. In some embodiments, monitoring further comprises measuring the expression level of PHGDH using said series of samples; and determining the longitudinal trend in the expression level of PHGDH.

In some embodiments, measuring the expression level of PHGDH is performed by measuring the amount of extracellular RNA (exRNA) produced from expression of PHGDH in the subject. In some embodiments, the exRNA is produced from transcription of the PHGDH gene. In some embodiments, the exRNA is mRNA or pre-mRNA. In some embodiments, at least one of the series of samples is a whole blood sample, a plasma sample, a serum sample, a saliva sample, a cell culture media sample, a urine sample, an amniotic fluid sample, a mucus sample, a semen sample, a vaginal fluid sample, a sputum sample, a cerebrospinal fluid sample, a lymphatic fluid sample, an ocular fluid sample, a sweat sample, or a stool sample. In some embodiments, at least one of the series of samples has a liquid volume of less than or equal to about 100 μl, about 50 μl, about 5 μl, or about 1 μl. In some embodiments, measuring the measuring the expression level of PHGDH is performed by SILVER-Seq technology.

In certain embodiments of the methods described herein, the neuro-excitotoxicity is resulted from overexcitation of an excitatory synaptic receptor upon binding of glycine and/or serine to the excitatory synaptic receptor. In some embodiments, the neuronal disease is resulted from death of neurons resulted from overexcitation of an excitatory synaptic receptor upon binding of glycine and/or serine to the excitatory synaptic receptor. In some embodiments, the neuronal disorder associated with neuro-excitotoxicity is resulted from overexcitation of NMDA receptors in the subject.

In certain embodiments of the methods described herein, the neuronal disorder is Alzheimer's disease, schizophrenia, amyotrophic lateral sclerosis (ALS), epilepsy, or drug addiction. In certain embodiments of the methods described herein, the neuronal disorder is Alzheimer's disease.

A number of embodiments of the invention have been described. Nevertheless, it will be understood that various modifications may be made without departing from the spirit and scope of the invention. Accordingly, the descriptions in the Experimental section and examples are intended to illustrate but not limit the scope of invention described in the claims.

7. EXPERIMENTAL

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

7.1 General Methods

The following materials and methods were used to carry out studies in the following examples.

7.1.1 Human Plasma Samples and SILVER-Seq Analysis of Human Plasma Samples

Plasma collection and analyses were approved by the University of California San Diego Human Research Protection Office. Every research subject or next of kin with guardianship of the subject, if necessary, who entered the UCSD Shiley-Marcos Alzheimer's Disease Research Center (ADRC) agreed to a postmortem examination as part of the entry criteria. Written informed consent was obtained from each participant. Venous blood was drawn by an ADRC staff member trained in phlebotomy. This blood was drawn in the morning (08:00-10:00) to minimize circadian variability of plasma analytes but fasting was not required. EDTA plasma was prepared by letting 2 samples (16 mL) stand in a vacutainer tube for 30 minutes, followed by centrifugation at room temperature at 3,500 g×15 minutes, and aliquoting the plasma into 0.5 mL aliquots in polypropylene cryotubes (0.5 mL, Sarstedt) to which barcoded labels were applied. Aliquots were then flash frozen and stored at −80° C. Thawed plasma was aliquoted into 5 µl per sample and was subjected to SILVER-seq. A total of 164 samples were sequenced to yield on average 19.2 million 75 bp single-end reads per sample. All sequencing data reported in this study has been deposited into Gene Expression Omnibus (GEO) under accession number GSE136243.

7.1.2 SILVER-Seq Data Processing

Adapters and low-quality bases were trimmed by Trimmomatic (version 0.36) [87]. The trimmed sequences were aligned to human reference genome (GRCh38/hg38) by STAR (version 2.5.4b) [88] and de-duplicated by UMI. Read counts per gene were calculated by featureCounts (version 1.6.1) [89] with the Ensembl gene annotation GTF file (release 84) and subsequently converted to Transcripts Per Million (TPM).

7.1.3 Retrieving the summary of tissue-specific expression from GTEx

The GTEx consortium's summary table of tissue specific expression was retrieved [52]. This summary table was based on GTEx consortium's definition of tissue-specific score (TS_Score), recommended threshold (TS_Score>3), and GTEx V6p data release that included 8,527 samples from 13 brain regions and 36 other tissues [52]. Based on this summary table, 1,514 brain-specific genes with TS_Score>3 in at least one brain region and TS_Score≤3 in all peripheral tissues were retrieved. To account for the recent data release, TS_Scores [52] based on the latest GTEx dataset (V8) were re-calculated, including 17,382 samples from 13 brain regions and 41 other tissues. TS_Scores based on young (age<60), old (age≥60), female, and male samples were separately calculated. The stronger criteria for defining brain specific expression were: TS_Score>3 in at least one brain region, and TS_Score≤3 in all peripheral tissues, and the average TPM of the 13 brain regions >0.1, and the maximum TPM of the 41 peripheral tissues <0.1.

7.1.4 Quantification of Transposon exRNA Expression Levels

The annotations of transposons, transposon clades was used as described previously [88]. Expression levels of transposons were calculated by SalmonTE (version 0.4) with default parameters [88].

7.1.5 RNA-Seq of AD and Control Brains

Pre-processed RNA-seq datasets of AD and control brains generated by the AMP-AD consortium were downloaded from AMP-AD Knowledge Portal (www.synapse.org/#!Synapse:syn9702085).

7.1.6 Serum exRNA Sequencing Data

The exRNA sequencing dataset of the Burgos study was downloaded from exRNA Atlas (exrna-atlas.org/) by accession ID EXR-KJENS1sPlvS2-AN [7]. The read counts on Gencode genes were produced by the ERCC consortium. As quality control, the samples with at least 1 mapped read (read count >0) on 9,500 or more genes were retained for further analysis. The read counts per gene were converted to normalized CPM (counts per million) values for downstream analyses [90].

7.1.7 AD-Associated Genes from DisGeNET Database

A total of 1,981 documented and 84 expert curated genes were downloaded from DisGeNet (www.disgenet.org/) by querying the gene-disease associations with "Alzheimer's Disease" [47]. Among them, 1,926 of the 1,981 documented and 83 of the 84 expert curated genes had Ensembl (GRCh38 release 84) gene IDs and were used in the analysis.

7.1.8 Published Proteomics Datasets

The processed proteomics dataset from the Hondius study was retrieved from their supplementary Table 2 [53]. The processed datasets of the Seyfried study and the Ping study were downloaded from the Synapse platform (www.synapse.org) by accession IDs syn3606086 and syn10239444, respectively [54, 55].

7.1.9 Statistical Analyses

All the statistical analyses were performed with R (version 3.6.0) [91]. T-test and ANOVA were carried out with the t.test( ) and aov( ) functions. FDR was calculated with the p.adjust( ) function. Pearson correlation was calculated with the cor( ) function. Linear regression was carried out with the lm( ) function. Linear mixed model analysis was implemented using the lme4 package in R [92].

7.1.10 Analysis of Longitudinal Changes by a Mixed Model

The mixed model was specified as:

$$y_{ij} = \beta_{0i} + \beta_{1i}A_{ij} + R_{ij}$$

and, $$\beta_{0i} = \gamma_{00} + \gamma_{01}G_i + \gamma_{02}S_i + U_{0i}$$

$$\beta_{1i} = \gamma_{10} + \gamma_{11}G_i + \gamma_{12}S_i$$

where, $$U_{0i} \sim \mathcal{N}(0, \tau_{00}^2)$$

$$R_{ij} \sim \mathcal{N}(0, \sigma^2)$$

In this model, the indices were i: research subject, and j: sample. The response variable was PHGDH's exRNA level:

Y. The observed data of the response variable was the log transformed TPM: log 2(TPM+1). The fixed effects were Time (A, age), Group (G, converter or control), and Sex (S, male or female). $\beta_{0i}$ was the intercept that accounts for group and sex, where $U_{0i}$ was the error term for each sample. $\beta_{1i}$ included the contribution of time to the intercept ($\gamma_{10} \times A_{ij}$), the interaction of group and time ($\gamma_{11}G_i \times A_{ij}$) and the interaction of sex and time ($\gamma_{12}S_i \times A_{ij}$). This model was implemented using the lme4 package in R [92].

7.1.11 Patient Population: A 15-Year Follow-Up Study of Sporadic AD

In order to generate longitudinal data on sporadic AD, archived plasma samples from research subjects being followed at the UCSD Shiley-Marcos Alzheimer's Disease Research Center during a 15-year period from 2000 to 2015 were selected. The criteria were subjects older than 70 years of age who were examined postmortem to confirm the clinical diagnosis of AD (pathology-confirmed participants); had multiple longitudinal blood samples spanning at least 4 years; and in cases who transitioned from normal cognitive status to mild cognitive impairment (MCI) or dementia during the course of the study, provided samples prior to the change in cognitive status. A total of 35 pathology-confirmed participants from this 15-year follow-up satisfied the criteria (Table 1).

TABLE 1

Summary of the 35 participants. Depending on their diagnoses, participants were split into three groups (Group column), namely AD, control, and converter. Braak stages were obtained from the pathological analysis of their postmortem brains (Braak stage). For converters, the time of MCI or AD diagnoses was provided (Year diagnosis).

| Donor ID | Group | Age at death | Sex | Braak stage | Year diagnosis | APOE status |
|---|---|---|---|---|---|---|
| N_1 | control | 86 | M | 1 | NA | ε3/ε4 |
| N_2 | control | 93 | F | 1 | NA | ε3/ε3 |
| N_3 | control | 86 | M | 1 | NA | ε2/ε3 |
| N_4 | control | 83 | M | 1 | NA | ε3/ε3 |
| N_5 | control | 89 | M | 2 | NA | ε3/ε3 |
| N_6 | control | 96 | F | 2 | NA | ε3/ε3 |
| N_7 | control | 83 | F | 2 | NA | ε3/ε4 |
| N_8 | control | 73 | F | 1 | NA | ε3/ε3 |
| N_9 | control | 94 | F | 2 | NA | ε2/ε3 |
| AD_1 | AD | 85 | F | 5 | NA | ε3/ε4 |
| AD_2 | AD | 86 | F | 4 | NA | ε3/ε3 |
| AD_3 | AD | 89 | M | 5 | NA | ε3/ε3 |
| AD_4 | AD | 82 | F | 6 | NA | ε3/ε3 |
| AD_5 | AD | 85 | M | 5 | NA | ε3/ε3 |
| AD_6 | AD | 88 | M | 6 | NA | ε2/ε3 |
| AD_7 | AD | 88 | M | 6 | NA | ε3/ε3 |
| AD_8 | AD | 87 | F | 5 | NA | ε3/ε4 |
| AD_9 | AD | 82 | F | 6 | NA | ε4/ε4 |
| AD_10 | AD | 90 | M | 6 | NA | ε4/ε4 |
| AD_11 | AD | 81 | M | 6 | NA | ε4/ε4 |
| AD_12 | AD | 71 | M | 6 | NA | ε3/ε3 |
| AD_13 | AD | 83 | F | 6 | NA | ε4/ε4 |
| AD_14 | AD | 87 | F | 4 | NA | ε3/ε3 |
| AD_15 | AD | 77 | M | 6 | NA | ε4/ε4 |
| C_1 | converter | 91 | F | 3 | 2010 | ε3/ε4 |
| C_2 | converter | 86 | M | 5 | 2012 | ε3/ε3 |
| C_3 | converter | 91 | F | 3 | 2006 | ε3/ε4 |
| C_4 | converter | 90 | F | 6 | 2007 | ε3/ε3 |
| C_5 | converter | 93 | F | 5 | 2005 | ε3/ε3 |
| C_6 | converter | 92 | M | 6 | 2012 | ε2/ε4 |
| C_7 | converter | 96 | F | 5 | 2011 | ε3/ε4 |
| C_8 | converter | 89 | M | 5 | 2006 | ε3/ε3 |
| C_9 | converter | 85 | F | 6 | 2006 | ε3/ε4 |
| C_10 | converter | 96 | F | 5 | 2007 | ε3/ε3 |
| C_11 | converter | 90 | F | 3 | 2008 | ε3/ε3 |

These included 9 cognitively normal subjects (controls), who were not cognitively impaired during the entire follow-up period and whose postmortem neuropathological analyses confirmed that they lacked AD-associated changes (top group lines, FIG. 1). Consistent with their advanced ages, postmortem examinations demonstrated Braak stage 1 or 2 for these individuals (Table 1). Two out the 9 controls carried one ε4 allele of the APOE gene, and the other 7 controls did not carry the ε4 allele.

There were 15 subjects who were clinically diagnosed as probable AD when they first enrolled and their postmortem examinations were consistent with a pathological diagnosis of AD with Braak stages 4 to 6 (red lines, FIG. 1) (Table 1). Five of the 15 AD subjects were homozygous for ε4, 2 AD subjects each carried a single ε4 allele, and the other 8 AD subjects did not carry the ε4 allele.

The third group of 11 "converters" were cognitively normal at enrollment but, during their longitudinal follow-up period, their clinical diagnoses were changed to MCI. Postmortem examination of these individuals showed AD changes with Braak stages between 3 to 6 (bottom group lines, FIG. 1) (Table 1). Five of the 11 converters carried a single ε4 allele, and the other 6 converters did not carry the ε4 allele. A total of 164 plasma samples were collected from these 35 participants (dots, FIG. 1).

7.2 Example 1: Correlation of the Expression of Brain-Specific Genes and Detection of these Genes in Plasma The 164 plasma samples were sequenced using the SILVER-seq technique as described in WO 2019/045803 (Table 2). Genome-wide distributions of the Transcripts Per Million (TPM) of known genes exhibited little difference between the earlier and later years of sample collection (FIG. 2).

TABLE 2

Summary of plasma samples and SILVER-seq libraries. Each plasma sample is given a Sample ID, which corresponded to a unique donor (Donor ID), and acquisition time (Sampling year). Each donor belonged to one of the three donor groups (Group): controls (N), AD (AD), and converters (C). The total (Total reads #), uniquely mapped (Uniquely mapped reads #), and de-duplicated uniquely mapped (Uniquely mapped # after de-duplication) numbers of each SILVER-seq library are listed.

| Sample ID | Donor ID | Group | Sampling year | Total reads # | Uniquely mapped reads # | Uniquely mapped # after de-duplication |
|---|---|---|---|---|---|---|
| N_1_01_1 | N_1 | N | 2001 | 19,594,807 | 15,960,731 | 4,402,421 |
| N_1_05_1 | N_1 | N | 2005 | 17,180,938 | 14,612,553 | 5,127,770 |
| N_1_07_1 | N_1 | N | 2007 | 17,899,720 | 15,598,141 | 6,882,351 |
| N_1_08_1 | N_1 | N | 2008 | 20,587,151 | 17,942,961 | 7,049,503 |
| N_1_09_1 | N_1 | N | 2009 | 19,249,974 | 16,786,038 | 5,984,756 |
| N_2_00_1 | N_2 | N | 2000 | 23,303,547 | 20,446,600 | 15,787,139 |
| N_2_01_1 | N_2 | N | 2001 | 21,976,682 | 19,219,973 | 9,226,811 |
| N_2_03_1 | N_2 | N | 2003 | 26,018,995 | 22,611,737 | 8,955,336 |
| N_2_06_1 | N_2 | N | 2006 | 21,014,159 | 18,496,974 | 7,293,615 |
| N_2_08_1 | N_2 | N | 2008 | 23,259,013 | 20,640,555 | 12,028,987 |
| N_3_01_1 | N_3 | N | 2001 | 19,706,761 | 17,350,461 | 10,915,465 |
| N_3_03_1 | N_3 | N | 2003 | 20,544,987 | 18,041,495 | 7,575,996 |
| N_3_04_1 | N_3 | N | 2004 | 13,668,783 | 11,986,435 | 4,647,423 |
| N_3_06_1 | N_3 | N | 2006 | 14,915,439 | 13,174,660 | 4,883,823 |
| N_4_01_1 | N_4 | N | 2001 | 24,945,016 | 21,790,351 | 2,070,274 |
| N_4_02_1 | N_4 | N | 2002 | 21,959,810 | 19,499,095 | 1,724,114 |
| N_4_04_1 | N_4 | N | 2004 | 13,212,206 | 11,572,707 | 4,248,611 |
| N_4_06_1 | N_4 | N | 2006 | 13,514,997 | 11,690,006 | 3,699,328 |
| N_4_08_1 | N_4 | N | 2008 | 14,576,003 | 12,947,550 | 4,195,057 |
| N_5_03_1 | N_5 | N | 2003 | 13,471,958 | 11,452,303 | 3,521,365 |

TABLE 2-continued

Summary of plasma samples and SILVER-seq libraries. Each
plasma sample is given a Sample ID, which corresponded to a
unique donor (Donor ID), and acquisition time (Sampling
year). Each donor belonged to one of the three donor groups
(Group): controls (N), AD (AD), and converters (C). The total
(Total reads #), uniquely mapped (Uniquely mapped reads #),
and de-duplicated uniquely mapped (Uniquely mapped # after
de-duplication) numbers of each SILVER-seq library are listed.

| Sample ID | Donor ID | Group | Sampling year | Total reads # | Uniquely mapped reads # | Uniquely mapped # after de-dupli-cation |
|---|---|---|---|---|---|---|
| N_5_04_1 | N_5 | N | 2004 | 14,010,147 | 12,251,312 | 5,212,685 |
| N_5_06_1 | N_5 | N | 2006 | 20,587,558 | 18,262,363 | 8,152,483 |
| N_5_08_1 | N_5 | N | 2008 | 18,803,331 | 16,349,540 | 6,336,351 |
| N_5_10_1 | N_5 | N | 2010 | 21,876,629 | 19,174,107 | 7,545,180 |
| N_6_01_1 | N_6 | N | 2001 | 24,135,291 | 20,663,811 | 5,713,482 |
| N_6_02_1 | N_6 | N | 2002 | 22,702,886 | 20,066,441 | 7,748,224 |
| N_6_03_1 | N_6 | N | 2003 | 24,989,326 | 21,947,956 | 8,736,553 |
| N_6_06_1 | N_6 | N | 2006 | 25,301,429 | 22,400,746 | 8,870,898 |
| N_6_08_1 | N_6 | N | 2008 | 26,670,911 | 23,567,381 | 9,616,161 |
| N_7_01_1 | N_7 | N | 2001 | 17,966,723 | 15,967,595 | 7,553,896 |
| N_7_02_1 | N_7 | N | 2002 | 18,340,167 | 16,232,030 | 6,230,976 |
| N_7_04_1 | N_7 | N | 2004 | 18,640,424 | 16,545,515 | 6,671,079 |
| N_7_07_1 | N_7 | N | 2007 | 14,203,060 | 12,680,980 | 6,005,048 |
| N_8_01_1 | N_8 | N | 2001 | 19,266,848 | 17,017,654 | 8,335,259 |
| N_8_05_1 | N_8 | N | 2005 | 18,850,462 | 16,557,254 | 4,761,558 |
| N_8_07_1 | N_8 | N | 2007 | 19,391,295 | 17,001,294 | 5,995,631 |
| N_9_00_1 | N_9 | N | 2000 | 19,669,124 | 17,438,690 | 7,305,551 |
| N_9_03_1 | N_9 | N | 2003 | 21,500,961 | 19,099,125 | 8,342,453 |
| N_9_06_1 | N_9 | N | 2006 | 19,726,257 | 17,150,950 | 3,998,254 |
| N_9_08_1 | N_9 | N | 2008 | 14,802,346 | 13,162,412 | 5,146,730 |
| N_9_12_1 | N_9 | N | 2012 | 21,389,640 | 19,007,167 | 8,462,188 |
| AD_1_02_1 | AD_1 | AD | 2002 | 15,802,617 | 14,039,516 | 4,987,525 |
| AD_1_04_1 | AD_1 | AD | 2004 | 15,165,386 | 13,473,080 | 4,814,367 |
| AD_1_08_1 | AD_1 | AD | 2008 | 15,329,635 | 13,686,628 | 5,549,721 |
| AD_1_09_1 | AD_1 | AD | 2009 | 18,167,246 | 16,182,622 | 6,570,307 |
| AD_1_11_1 | AD_1 | AD | 2011 | 16,975,048 | 15,245,143 | 7,653,286 |
| AD_1_13_1 | AD_1 | AD | 2013 | 17,764,070 | 15,834,288 | 5,391,798 |
| AD_2_01_1 | AD_2 | AD | 2001 | 23,582,183 | 20,822,211 | 7,366,716 |
| AD_2_02_1 | AD_2 | AD | 2002 | 21,609,124 | 19,222,014 | 7,159,157 |
| AD_2_03_1 | AD_2 | AD | 2003 | 22,569,939 | 20,083,336 | 7,364,408 |
| AD_2_05_1 | AD_2 | AD | 2005 | 23,172,958 | 20,825,625 | 8,047,764 |
| AD_2_07_1 | AD_2 | AD | 2007 | 21,370,488 | 18,966,467 | 7,029,084 |
| AD_3_00_1 | AD_3 | AD | 2000 | 21,244,289 | 18,424,934 | 8,284,127 |
| AD_3_01_1 | AD_3 | AD | 2001 | 20,763,826 | 17,888,452 | 15,045,925 |
| AD_3_03_1 | AD_3 | AD | 2003 | 22,649,948 | 19,876,432 | 8,146,615 |
| AD_3_05_1 | AD_3 | AD | 2005 | 17,346,731 | 15,075,192 | 4,410,514 |
| AD_3_07_1 | AD_3 | AD | 2007 | 21,374,241 | 18,806,841 | 12,609,665 |
| AD_4_10_1 | AD_4 | AD | 2010 | 16,244,208 | 14,453,455 | 5,697,360 |
| AD_4_11_1 | AD_4 | AD | 2011 | 17,009,419 | 15,109,014 | 5,159,341 |
| AD_4_12_1 | AD_4 | AD | 2012 | 17,274,012 | 15,292,932 | 4,764,882 |
| AD_4_13_1 | AD_4 | AD | 2013 | 14,517,003 | 12,791,168 | 4,175,583 |
| AD_5_09_1 | AD_5 | AD | 2009 | 22,134,410 | 19,594,159 | 6,545,862 |
| AD_5_10_1 | AD_5 | AD | 2010 | 25,108,292 | 22,188,305 | 6,536,391 |
| AD_5_11_1 | AD_5 | AD | 2011 | 20,366,315 | 17,786,260 | 4,612,111 |
| AD_5_12_1 | AD_5 | AD | 2012 | 20,021,636 | 17,707,330 | 5,679,729 |
| AD_5_13_1 | AD_5 | AD | 2013 | 21,535,845 | 19,135,181 | 7,032,302 |
| AD_6_09_1 | AD_6 | AD | 2009 | 17,228,824 | 15,304,888 | 5,811,057 |
| AD_6_10_1 | AD_6 | AD | 2010 | 13,864,444 | 12,167,491 | 4,733,356 |
| AD_6_11_1 | AD_6 | AD | 2011 | 13,616,271 | 11,689,968 | 3,138,274 |
| AD_6_12_1 | AD_6 | AD | 2012 | 15,671,324 | 13,854,563 | 3,235,239 |
| AD_6_13_1 | AD_6 | AD | 2013 | 17,454,659 | 15,129,133 | 13,052,351 |
| AD_7_06_1 | AD_7 | AD | 2006 | 17,179,652 | 15,113,513 | 6,063,115 |
| AD_7_08_1 | AD_7 | AD | 2008 | 16,692,123 | 14,610,388 | 5,163,759 |
| AD_7_09_1 | AD_7 | AD | 2009 | 18,525,990 | 16,316,868 | 7,650,530 |
| AD_7_11_1 | AD_7 | AD | 2011 | 19,485,337 | 17,078,138 | 5,081,888 |
| AD_7_12_1 | AD_7 | AD | 2012 | 19,107,258 | 16,497,658 | 7,783,463 |
| AD_8_03_1 | AD_8 | AD | 2003 | 18,086,598 | 16,035,418 | 7,718,649 |
| AD_8_05_1 | AD_8 | AD | 2005 | 15,972,332 | 14,380,355 | 4,345,991 |
| AD_8_07_1 | AD_8 | AD | 2007 | 15,949,404 | 14,103,385 | 5,464,220 |
| AD_8_09_1 | AD_8 | AD | 2009 | 14,270,887 | 12,656,115 | 4,963,642 |
| AD_8_11_1 | AD_8 | AD | 2011 | 24,591,782 | 21,987,230 | 2,424,444 |
| AD_8_12_1 | AD_8 | AD | 2012 | 19,368,341 | 17,046,364 | 8,105,987 |
| AD_9_04_1 | AD_9 | AD | 2004 | 15,748,188 | 13,770,701 | 4,239,703 |
| AD_9_06_1 | AD_9 | AD | 2006 | 18,472,225 | 16,353,192 | 7,214,932 |
| AD_9_09_1 | AD_9 | AD | 2009 | 17,755,963 | 15,904,009 | 7,192,253 |

TABLE 2-continued

Summary of plasma samples and SILVER-seq libraries. Each
plasma sample is given a Sample ID, which corresponded to a
unique donor (Donor ID), and acquisition time (Sampling
year). Each donor belonged to one of the three donor groups
(Group): controls (N), AD (AD), and converters (C). The total
(Total reads #), uniquely mapped (Uniquely mapped reads #),
and de-duplicated uniquely mapped (Uniquely mapped # after
de-duplication) numbers of each SILVER-seq library are listed.

| Sample ID | Donor ID | Group | Sampling year | Total reads # | Uniquely mapped reads # | Uniquely mapped # after de-dupli-cation |
|---|---|---|---|---|---|---|
| AD_10_04_1 | AD_10 | AD | 2004 | 17,407,558 | 15,143,195 | 4,152,688 |
| AD_10_06_1 | AD_10 | AD | 2006 | 15,848,749 | 13,760,564 | 4,742,336 |
| AD_10_09_1 | AD_10 | AD | 2009 | 18,450,367 | 16,316,813 | 8,522,286 |
| AD_10_10_1 | AD_10 | AD | 2010 | 17,507,157 | 15,526,211 | 8,873,726 |
| AD_11_02_1 | AD_11 | AD | 2002 | 15,609,887 | 13,619,477 | 4,191,414 |
| AD_11_03_1 | AD_11 | AD | 2003 | 22,370,398 | 18,958,890 | 2,782,171 |
| AD_11_04_1 | AD_11 | AD | 2004 | 17,047,615 | 14,910,104 | 5,179,333 |
| AD_11_08_1 | AD_11 | AD | 2008 | 21,290,609 | 17,468,489 | 3,259,662 |
| AD_11_10_1 | AD_11 | AD | 2010 | 17,498,437 | 14,488,284 | 3,445,709 |
| AD_12_02_1 | AD_12 | AD | 2002 | 17,250,101 | 15,166,360 | 7,163,568 |
| AD_12_03_1 | AD_12 | AD | 2003 | 15,170,091 | 13,153,295 | 4,475,399 |
| AD_12_05_1 | AD_12 | AD | 2005 | 24,541,790 | 21,571,749 | 8,904,830 |
| AD_12_07_1 | AD_12 | AD | 2007 | 15,214,927 | 13,290,324 | 4,842,761 |
| AD_13_00_1 | AD_13 | AD | 2000 | 13,871,422 | 11,883,178 | 3,960,933 |
| AD_13_03_1 | AD_13 | AD | 2003 | 15,328,293 | 13,866,120 | 3,672,817 |
| AD_13_04_1 | AD_13 | AD | 2004 | 14,108,861 | 12,569,478 | 4,232,684 |
| AD_13_06_1 | AD_13 | AD | 2006 | 15,455,470 | 13,378,444 | 3,634,266 |
| AD_14_00_1 | AD_14 | AD | 2000 | 21,222,925 | 18,749,500 | 8,395,708 |
| AD_14_01_1 | AD_14 | AD | 2001 | 21,675,990 | 19,201,017 | 8,932,157 |
| AD_14_03_1 | AD_14 | AD | 2003 | 20,962,968 | 18,602,579 | 7,955,035 |
| AD_14_05_1 | AD_14 | AD | 2005 | 21,581,496 | 19,151,282 | 7,843,308 |
| AD_14_07_1 | AD_14 | AD | 2007 | 21,154,863 | 18,752,134 | 8,114,993 |
| AD_14_10_1 | AD_14 | AD | 2010 | 21,902,270 | 19,181,660 | 7,195,912 |
| AD_14_13_1 | AD_14 | AD | 2013 | 23,559,753 | 21,021,350 | 10,349,266 |
| AD_14_14_1 | AD_14 | AD | 2014 | 20,449,036 | 18,224,766 | 7,903,020 |
| AD_15_00_1 | AD_15 | AD | 2000 | 15,638,741 | 13,513,589 | 4,130,037 |
| AD_15_01_1 | AD_15 | AD | 2001 | 16,844,487 | 14,612,328 | 3,709,906 |
| AD_15_03_1 | AD_15 | AD | 2003 | 13,522,678 | 11,412,606 | 3,063,814 |
| AD_15_04_1 | AD_15 | AD | 2004 | 19,285,074 | 16,954,801 | 8,331,351 |
| AD_15_06_1 | AD_15 | AD | 2006 | 20,007,400 | 17,496,482 | 7,105,986 |
| C_1_01_1 | C_1 | C | 2001 | 61,231,966 | 51,901,026 | 10,941,150 |
| C_1_03_1 | C_1 | C | 2003 | 13,959,140 | 12,138,914 | 3,824,939 |
| C_1_04_1 | C_1 | C | 2004 | 16,664,901 | 14,718,358 | 6,987,729 |
| C_1_08_1 | C_1 | C | 2008 | 22,525,447 | 19,742,304 | 2,346,542 |
| C_1_11_1 | C_1 | C | 2011 | 25,167,766 | 21,945,888 | 3,691,692 |
| C_1_12_1 | C_1 | C | 2012 | 24,384,038 | 22,111,928 | 3,825,427 |
| C_2_07_1 | C_2 | C | 2007 | 16,534,523 | 14,413,162 | 5,316,468 |
| C_2_09_1 | C_2 | C | 2009 | 14,574,446 | 12,587,151 | 3,933,262 |
| C_2_10_1 | C_2 | C | 2010 | 14,650,667 | 12,897,873 | 4,076,061 |
| C_2_11_1 | C_2 | C | 2011 | 14,762,276 | 13,011,937 | 4,473,125 |
| C_2_12_1 | C_2 | C | 2012 | 13,661,726 | 11,701,190 | 3,738,496 |
| C_3_02_1 | C_3 | C | 2002 | 23,445,729 | 20,696,424 | 7,665,689 |
| C_3_04_1 | C_3 | C | 2004 | 22,994,507 | 20,613,793 | 11,176,609 |
| C_3_06_1 | C_3 | C | 2006 | 19,271,078 | 17,052,427 | 6,101,766 |
| C_4_03_1 | C_4 | C | 2003 | 23,036,796 | 20,314,939 | 7,239,735 |
| C_4_05_1 | C_4 | C | 2005 | 21,565,874 | 19,219,942 | 10,887,358 |
| C_4_07_1 | C_4 | C | 2007 | 20,580,853 | 18,209,461 | 7,287,524 |
| C_5_01_1 | C_5 | C | 2001 | 20,447,585 | 18,015,573 | 14,348,276 |
| C_5_02_1 | C_5 | C | 2002 | 20,498,270 | 18,305,196 | 8,644,680 |
| C_5_05_1 | C_5 | C | 2005 | 18,616,354 | 16,748,456 | 10,260,296 |
| C_5_07_1 | C_5 | C | 2007 | 18,536,095 | 16,487,732 | 10,000,800 |
| C_6_06_1 | C_6 | C | 2006 | 19,471,875 | 16,885,139 | 8,887,307 |
| C_6_08_1 | C_6 | C | 2008 | 20,705,421 | 18,107,283 | 6,994,894 |
| C_6_12_1 | C_6 | C | 2012 | 19,790,433 | 16,959,001 | 7,986,879 |
| C_6_13_1 | C_6 | C | 2013 | 20,697,510 | 17,827,213 | 7,749,291 |
| C_7_00_1 | C_7 | C | 2000 | 16,322,007 | 14,214,730 | 4,598,941 |
| C_7_01_1 | C_7 | C | 2001 | 16,591,535 | 14,527,078 | 5,024,269 |
| C_7_04_1 | C_7 | C | 2004 | 20,066,880 | 17,644,401 | 5,963,155 |
| C_7_08_1 | C_7 | C | 2008 | 17,463,286 | 14,963,709 | 4,704,684 |
| C_8_00_1 | C_8 | C | 2000 | 22,944,956 | 20,157,031 | 6,569,538 |
| C_8_01_1 | C_8 | C | 2001 | 16,422,185 | 14,265,483 | 3,760,799 |
| C_8_03_1 | C_8 | C | 2003 | 15,402,911 | 13,404,314 | 4,899,142 |
| C_8_04_1 | C_8 | C | 2004 | 20,270,744 | 17,819,449 | 7,309,193 |
| C_8_06_1 | C_8 | C | 2006 | 15,813,120 | 14,090,741 | 3,349,299 |
| C_9_00_1 | C_9 | C | 2000 | 21,925,864 | 19,293,292 | 3,130,919 |

TABLE 2-continued

Summary of plasma samples and SILVER-seq libraries. Each
plasma sample is given a Sample ID, which corresponded to a
unique donor (Donor ID), and acquisition time (Sampling
year). Each donor belonged to one of the three donor groups
(Group): controls (N), AD (AD), and converters (C). The total
(Total reads #), uniquely mapped (Uniquely mapped reads #),
and de-duplicated uniquely mapped (Uniquely mapped # after
de-duplication) numbers of each SILVER-seq library are listed.

| Sample ID | Donor ID | Group | Sampling year | Total reads # | Uniquely mapped reads # | Uniquely mapped # after de-duplication |
|---|---|---|---|---|---|---|
| C_9_05_1 | C_9 | C | 2005 | 23,996,254 | 20,705,191 | 6,520,245 |
| C_9_07_1 | C_9 | C | 2007 | 19,853,488 | 17,601,684 | 4,589,502 |
| C_9_10_1 | C_9 | C | 2010 | 19,460,640 | 17,147,347 | 7,367,669 |
| C_10_01_1 | C_10 | C | 2001 | 16,393,643 | 14,247,343 | 3,577,391 |
| C_10_03_1 | C_10 | C | 2003 | 13,654,416 | 11,905,382 | 4,107,855 |
| C_10_05_1 | C_10 | C | 2005 | 22,701,426 | 19,393,613 | 4,425,493 |
| C_10_08_1 | C_10 | C | 2008 | 21,036,919 | 18,555,244 | 5,331,816 |
| C_10_10_1 | C_10 | C | 2010 | 14,930,783 | 12,984,126 | 3,869,086 |
| C_10_13_1 | C_10 | C | 2013 | 16,179,193 | 13,838,596 | 3,540,091 |
| C_10_14_1 | C_10 | C | 2014 | 20,006,882 | 17,468,916 | 5,933,616 |
| C_11_01_1 | C_11 | C | 2001 | 15,773,586 | 13,808,261 | 5,085,145 |
| C_11_03_1 | C_11 | C | 2003 | 16,001,592 | 13,938,521 | 3,330,252 |
| C_11_04_1 | C_11 | C | 2004 | 21,130,010 | 19,087,296 | 4,383,438 |
| C_11_09_1 | C_11 | C | 2009 | 14,789,994 | 13,046,650 | 4,510,792 |

To check whether the expression level of a brain-specific gene in the brain correlated with the chance of this gene being detected in plasma by SILVER-seq, 1,514 brain-specific genes from GTEx consortium's summary of tissue-specific genes, which is based on GTEx consortium's definition of tissue-specific score (TS_Score) and recommended threshold (TS_Score>3) [52] were retrieved. These retrieved brain-specific genes were categorized by their average TPM in GTEx assayed brain regions from low to high into four groups, that were TPM=(0,1], (1,10], (10,100], and (100, infinity) (FIG. 3A). The odds ratio of the brain-specific genes in each group and those genes detected in plasma increased as the average brain expression levels increased from group 1 to group 4 (FIG. 3B and Table 3), suggesting that the brain expression level of a brain-specific gene is positively correlated with the chances of detecting this gene in plasma. This positive correlation was not abolished by changing the threshold for determining what genes are detected in plasma (SILVER-seq's TPM>3, FIG. 4A).

TABLE 3

Calculation of the odds ratio between the brain-specific genes
in each expression group and the SILVER-seq detected genes from
a plasma sample. This table documents the number of brain-specific
genes in each expression group (rows) and the number of other
genes (last row) that are detected (left column) or not detected
(right column) in a plasma sample. The odds ratio of brain-specific
genes in the first group (brain average TPM within (0, 1]) and
SILVER-seq detected genes is calculated as (a11/a21)/(a51/a15).
The odds ratio of brain-specific genes in the second expression
group (brain average TPM within (1, 10]) and SILVER-seq detected
genes is calculated as (a21/a22)/(a51/a15).

| | | SILVER-seq TPM > 5 | TPM ≤ 5 |
|---|---|---|---|
| Brain-specific genes | (0, 1] | a11 = 154 | a12 = 463 |
| | (1, 10] | a21 = 115 | a22 = 227 |
| | (10, 100] | a31 = 186 | a32 = 192 |
| | (100, Inf) | a41 = 107 | a42 = 70 |
| Other genes | | a51 = 17270 | a15 = 42345 |

To test whether sex and age affect the aforementioned correlation, we identified brain-specific genes in male, female, young, and old subjects based on the latest GTEx data (GTEx V8) and GTEx consortium's recommended threshold for defining tissue specificity (TS_Score>3) [52] (FIG. 4B). The odds ratio of the male brain-specific genes in each expression group and those genes detected in male plasma samples increased as the average male brain expression levels increased from group 1 to group 4 (FIG. 4C). This positive correlation was repeated in the brain-specific genes identified from female subjects (FIG. 4D) and those shared by male and female, young and old GTEx research subjects (FIG. 4E).

Furthermore, we used stronger criteria for calling brain specific expression from GTEx V8 data, which led to 106 genes. We termed these 106 genes "brain-exclusive genes" and divided them into four expression quartiles based on each gene's average TPM in the GTEx assayed brain regions. The odds ratio of the brain-exclusive genes in each expression quartile and those genes detected in plasma increased from the lowest to the highest quartile (FIG. 4F). In comparison, when we re-ordered the brain-exclusive genes by each gene's average TPM of the 41 peripheral tissues, the odds ratio became invariant from quartile to quartile, suggesting the chances of detecting these genes in plasma were not driven by their expression levels in peripheral tissues (FIG. 4G). Taken together, and the higher the level of brain expression of a brain-specific gene, the greater the chance of this gene being detected by SILVER-seq in plasma.

7.3 Example 2: Lack of Genome-Wide Correlations of AD-Associated Changes Between Brain Gene Expression and Plasma exRNA Levels To test if there were genome-wide correlations of AD-associated gene expression changes in brain and exRNA changes in plasma, 6 RNA-seq datasets from 6 AD-related brain regions were re-analyzed. These datasets were generated from 3 donor cohorts by the AMP-AD consortium (Table 4) [50, 51].

TABLE 4

Summary of RNA-seq datasets generated by the National Institute
of Ageing (NIA)'s Accelerating Medicines Partnership-Alzheimer's
Disease (AMP-AD) program. Six RNA-seq datasets (Dataset #) from
3 donor cohorts (Cohort) including both AD (AD donors) and
control donors (Controls) from 6 AD-pathology-related brain
regions (Brain region) are included.

| Dataset # | Cohort | Brain region | # AD donors | # Controls |
|---|---|---|---|---|
| 1 | Mayo | temporal cortex | 80 | 74 |
| 2 | Mount Sinai | anterior prefrontal cortex | 85 | 67 |
| 3 | Mount Sinai | superior temporal gyrus | 75 | 53 |
| 4 | Mount Sinai | parahippocampal gyrus | 60 | 55 |
| 5 | Mount Sinai | inferior frontal gyrus | 73 | 55 |
| 6 | ROSMAP | dorsolateral prefrontal cortex | 155 | 86 |

The T statistic was used to represent the difference between AD and normal samples for each exRNA and the t-statistics between plasma and each brain region were compared (FIG. 5). The AD-associated plasma exRNA changes did not exhibit a genome-wide correlation to AD-associated changes in any analyzed brain region (all Pearson correlations <0.04). The lack of genome-wide correlations was expected because plasma exRNAs come from many tissues other than the brain. Even if AD can influence plasma exRNA levels, AD is only one of many physiological and pathological conditions that may have such influences. All these physiological and pathological conditions cannot be controlled for in the research subjects in AMP-AD and this study. In addition, there were significant technical differences on the experimental procedures for sequencing intracellular and extracellular RNAs. The lack of genome-wide correlations served as an important baseline to the rest of the analyses.

7.4 Example 3: Brain Transposon Activation in AD Detectable in Plasma exRNA

It was next tested whether the genes reported to be reliably overexpressed in AD brains as compared to control brains also exhibited higher exRNA levels in AD plasma as compared to control plasma. Among all transposon clades and families, the ERV1 clade of transposons exhibited the largest AD-vs-control expression difference in dorsolateral prefrontal cortex (DPC), an AD-affected brain region [43]. The t-statistic from that study [43] was re-plotted, comparing AD and control DPCs for every ERV1 transposon (dots, FIG. 6A). The distribution of these t-statistics shifted to above 0 (box plot, FIG. 6A) (p-value <2.2×10-16, t test), consistent with the previous report of higher expression of ERV1 transposons overall in AD brains [43]. Next, the t-statistic for every ERV1 transposon was calculated to compare AD and control plasma. The distribution of these plasma-derived t-statistics shifted to above 0 (FIG. 6B), suggesting that ERV1 derived exRNAs were more abundant in AD plasma than control plasma (p-value=1.02×10-5, t test). Thus, the exRNAs of the ERV1 clade of transposons detectable in plasma mirrored the pattern of overexpression reported in AD brains from a separate cohort. In comparison, among all analyzed transposon clades, the SINEs as a group exhibited the least AD-vs-control difference in brains [43]. Consistently, the SINE derived exRNAs as a group did not exhibit AD-to-control differences in plasma (p-value=0.903, t test) (FIG. 6B).

Although not a single transposable element on its own was reported to be consistently expressed at higher levels in AD brains (it was rather a pattern of increased overall transposon activity), the possibility of a single transposable element exhibiting consistent upregulation in brain and in plasma was nevertheless examined. Two out of the top 3 AD-upregulated ERV1 transposons in brain [43] did not exhibit clear changes in plasma (circled dots, FIGS. 6A and 6B). However, PRIMA4_LTR (red dot, FIG. 6A) [43], was indeed among the top ranked AD-upregulated ERV1 transposons in plasma (red dot, FIG. 6B), with a consistent exRNA change in plasma (p-value=0.031, ANOVA controlling for sex and APOE status) (FIG. 6C). These data suggest a specific transposable element with consistent AD-associated upregulation in brain and in plasma.

7.5 Example 4: Modest Consistency of AD-Associated Increases of mRNAs in the Brain and Plasma To test whether the coding genes with reported AD-associated expression changes in the brain exhibited corresponding changes in plasma, 6 RNA-seq datasets from 6 AD-related brain regions were re-analyzed. These datasets were generated from 3 donor cohorts by the AMP-AD consortium (Table 4) [50, 51]. A total of 28 coding genes were upregulated in at least 5 of these 6 brain regions in AD (FDR<0.05 in each brain region), which hereafter will be referred to as the AMP-AD genes. The T statistic was used to represent the exRNA difference between AD plasma and control plasma for every gene. The average T statistics of the AMP-AD genes was greater than that of all the genes (AMP-AD and All lanes, FIG. 7A). However, this difference was not statistically significant (p-value=0.141, permutation test), presumably due to the small number (28) of AMP-AD genes.

Next, a total of 1,375 genes associated with "lipid metabolic process" (GO:0006629) [48, 49] were retrieved. The average T statistics of the lipid metabolic process genes was greater than that of all the genes (p-value <0.0001, permutation test), suggesting an overall exRNA increase of lipid metabolic process genes in AD plasma. Twenty of these lipid metabolic process genes were genetically associated with AD (Lipid-AD lane, FIG. 7A), in which ACHE, APOE, ESR1, and APP ranked as the top 4 exRNAs with the largest increase in AD plasma as compared to control plasma (Table 5). However, none of them exhibited a statistically significant difference (smallest FDR=0.28, ANOVA controlling for sex and APOE genetic status) (Table 5).

TABLE 5

Comparison of exRNA levels between AD and controls on the 20 lipid metabolic process genes that were genetically associated with AD. ANOVA was used to control for sex and APOE genetic status.

| Gene | Gene ID | T-statistic (AD vs control) | Log2FC (AD vs control) | FDR (t-test) | FDR (ANOVA) |
|---|---|---|---|---|---|
| ACHE | ENSG00000087085 | 1.820 | 0.448 | 0.374 | 0.280 |
| APOE | ENSG00000130203 | 1.794 | 0.622 | 0.374 | 0.454 |
| ESR1 | ENSG00000091831 | 1.705 | 0.309 | 0.374 | 0.454 |
| APP | ENSG00000142192 | 1.644 | 0.283 | 0.374 | 0.440 |
| CRH | ENSG00000147571 | 1.616 | 0.625 | 0.374 | 0.280 |
| SORL1 | ENSG00000137642 | 1.602 | 0.246 | 0.374 | 0.280 |
| IL1B | ENSG00000125538 | 1.017 | 0.252 | 0.889 | 0.280 |
| CYP46A1 | ENSG00000036530 | 0.872 | 0.164 | 0.963 | 0.440 |
| PLCG2 | ENSG00000197943 | 0.728 | 0.127 | 0.986 | 0.462 |
| CLU | ENSG00000120885 | 0.479 | 0.093 | 0.986 | 0.539 |
| TPP1 | ENSG00000166340 | 0.442 | 0.095 | 0.986 | 0.810 |
| LEP | ENSG00000174697 | 0.394 | 0.116 | 0.986 | 0.462 |
| TNF | ENSG00000232810 | 0.272 | 0.075 | 0.986 | 0.454 |
| DHCR24 | ENSG00000116133 | 0.157 | 0.037 | 0.986 | 0.481 |
| ATP5A1 | ENSG00000152234 | 0.070 | 0.013 | 0.986 | 0.633 |
| CYP2D6 | ENSG00000100197 | 0.022 | 0.010 | 0.986 | 0.917 |
| INS | ENSG00000254647 | −0.017 | −0.011 | 0.986 | 0.907 |
| BAX | ENSG00000087088 | −0.129 | −0.037 | 0.986 | 0.860 |
| F2 | ENSG00000180210 | −0.218 | −0.062 | 0.986 | 0.759 |
| PPARG | ENSG00000132170 | −0.366 | −0.220 | 0.986 | 0.865 |

Taken together, the analyses of 4 gene groups including ERV1 and SINE transposons and lipid metabolic process and AMP-AD genes suggest that the brain upregulated AD-related transcripts exhibited weak but consistent trends of exRNA increases in AD plasma.

7.6 Example 5: Phosphoglycerate Dehydrogenase (PHGDH) Exhibited the Largest AD-Associated Increase in Plasma and Consistent Upregulation in Brain The AMP-AD gene with the largest AD-associated exRNA increase in plasma was phosphoglycerate dehydrogenase (PHGDH) (last bar on the right, FIG. 7B). PHGDH exhibited higher expression in AD patients (right bars) than control donors (left bars) in 5 brain regions including temporal cortex, dorsolateral prefrontal cortex, superior temporal gyms, parahippocampal gyms, and inferior frontal gyms (* marked columns, FIG. 7C), based on the AMP RNA-seq datasets (Table 4) [50] [51]. Although PHGDH also exhibited increased expression in anterior prefrontal cortex, it did not reach the significant cutoff of FDR<0.05 (last column, FIG. 7B). In plasma, PHGDH exRNA was more abundant in AD subjects as compared to age-matched controls (FDR=0.023, ANOVA controlling for sex and APOE status) (FIG. 7D). Accordingly, there were consistent changes in brain and in plasma and there was a large expression difference of plasma PHGDH between sporadic AD and controls.

7.7 Example 6: External Validation: Global Correlations

In order to externally validate the identified AD-versus-control increase of PHGDH exRNA, another research cohort with published exRNA sequencing data from 30 AD and 41 control serum samples (hereafter referred to as the Burgos dataset) [8] was used. Note that there were significant technical differences between the Burgos study and this current study, including the criteria for inclusion of research subjects, liquid biopsy type (the Burgos study used serum; the current study we used plasma), and the actual techniques for exRNA sequencing. To establish a baseline, it was tested if there was a global correlation of AD-associated exRNA changes between the two cohorts. To this end, the t-statistic was used to represent the difference between AD and normal samples for each exRNA and the t-statistics between the two cohorts was compared. The two cohorts did not exhibit a genome-wide correlation (Pearson correlation <0.01, FIG. 4E). This lack of global correlation could be attributable to at least two probable causes. Either AD does not induce global changes of exRNA levels or the technical differences make global correlations undetectable. Furthermore, as expected, the AD-associated serum exRNA changes did not exhibit a global correlation with AD-associated gene expression changes in any of the 6 analyzed brain regions (FIG. 5B). The lack of global correlations is an important baseline characteristic of the data, likely reflecting the compounded effects of many contributing factors to exRNA profiles.

7.8 Example 7: External Validation of AD-Versus-Control Differences of PHGDH exRNA The lack of a global correlation did not rule out the possibility that AD affected the exRNA profiles of a subset of genes. To test whether the genes that have been associated with AD by genetic association studies exhibited any correlated AD-versus-control changes between the two cohorts, the DisGeNET database [47] that integrated genotype-phenotype relationship datasets including GWAS data from multiple databases was leveraged. DisGeNET documented a total of 1,926 AD-associated genes, among which 83 genes had been reviewed by experts and were termed "expert curated" AD-associated genes. The 1,926 genes did not exhibit correlated changes between the two cohorts (Pearson correlation=0.018, p-value=0.43, FIG. 7F), although the Pearson correlation was approximately 2-fold larger than that of the all genes (Pearson correlation=0.009). Moreover, the 83 expert curated genes were not completely uncorrelated between the two cohorts (Pearson correlation=0.287, p-value=0.009, FIG. 7G). These increasing correlations from all genes to expert curated genes suggested that despite significant technical differences, AD-versus-control changes from two cohorts were not completely uncorrelated on the subset of genes that are relevant to AD.

For an external validation, the PHGDH exRNA levels in AD and control samples from the Burgos dataset were checked. PHGDH exRNA was upregulated in AD sera than control sera in the Burgos cohort (Fold change=2.4, t-test p-value=0.095). There was no multiple hypothesis testing in this case. Compared to the 1,926 DisGeNET documented AD-associated genes, PHGDH was among the most reproducibly upregulated exRNAs in both cohorts (p-value=1.8×10-5, permutation test) (FIG. 7F, FIGS. 8A and 8B). Compared to the 83 expert curated genes, PHGDH was also among the most reproducibly upregulated exRNAs in both cohorts (p-value <0.0001, permutation test) (FIG. 7G, FIGS. 8C and 8D). Taken together, PHGDH exRNA was increased in AD in both cohorts. No other AD-associated gene in the DisGeNET database exhibited a statistically significant and reproducible increase in these two cohorts.

7.9 Example 8: PHGDH Protein Changes in 5 AD Brain Regions from 4 Cohorts

Taking the above analyses together, PHGDH was the only gene that exhibited consistent AD-versus-control increases from multiple brain regions and plasma/serum in the total of 5 independent cohorts (3 AMP-AD cohorts, our cohort, and Burgos cohort). To test if brain PHGDH protein levels were changed in AD, 3 published proteomics studies were re-analzyed. Each study examined 1 or 2 brain regions, which were hippocampus [53], dorsolateral prefrontal cortex and precuneus [54], anterior cingulate gyms and frontal cortex [55] (Table 6).

TABLE 6

Summary of the 3 proteomics studies. The number of research
samples analyzed in each study (Study column), categorized by
brain regions (Brain regions), and phenotypes (other columns).

| Study | # of cohorts | Brain regions | Braak 0 | Braak 1-2 | Braak 3-4 | Braak 5-6 |
|---|---|---|---|---|---|---|
| Hondius et al. | 2 | Hippocampus | 5 | 12 | 12 | 11 |

| Study | # of cohorts | Brain regions | Control | Asymptomatic AD | AD | |
|---|---|---|---|---|---|---|
| Seyfried et al. | 1 | Dorsolateral prefrontal cortex | 12 | 13 | 17 | |
| | | Precuneus | 14 | 14 | 19 | |

| Study | # of cohorts | Brain regions | Control | PD | AD&PD | AD |
|---|---|---|---|---|---|---|
| Ping et al. | 1 | Anterior cingulate gyrus | 10 | 10 | 10 | 10 |
| | | Frontal cortex | 10 | 10 | 10 | 10 |

PD: Parkinson's disease.
AD&PD: AD and PD co-morbid.

Hippocampal PHGDH protein levels increased with Braak stages (ANOVA p-value=7.5×10-7) (FIG. 7H). Both dorsolateral prefrontal cortex and precuneus PHGDH protein levels exhibited sequential increases from controls to asymptomatic AD (intact cognition subjects who exhibited AD lesions at autopsy) and to symptomatic AD (p-value=0.045, two-way ANOVA) (FIGS. 7I and 7J). In addition, both anterior cingulate gyms and frontal cortex PHDGH protein levels were significantly increased in AD subjects (p-value <8×10-5) and in AD and Parkinson disease (AD&PD) co-morbid subjects as compared to controls (p-value <0.001, t test) (FIGS. 7K and 7L). Taken together, PHGDH protein exhibited significant increases in all 5 analyzed brain regions from 4 independent cohorts.

7.10 Example 9: Difference of PHGDH Protein Changes in AD and Parkinson Disease (PD)

It was tested whether brain PHDGH exhibited similar protein expression changes in PD as in AD. PD-versus-control PHDGH protein differences were much smaller than AD-versus-control differences or AD&PD-versus control differences in anterior cingulate gyms (FIG. 7K). Frontal cortex PHGDH protein levels did not exhibit a significant difference between PD and controls (p-value=0.87, t test), but significant AD-versus-control and AD&PD-versus-control differences (FIG. 7L). These data suggested a disease-type specificity of brain PHGDH levels.

7.11 Example 10: Longitudinal Changes of Plasma PHGDH exRNA Differentiate Converters from Controls To evaluate whether plasma PHGDH could be used as a pre-symptomatic biomarker for AD-related cognition impairment, the longitudinal data from the converter group of 11 subjects was utilized, from which the majority of the plasma samples were collected prior to each subject's diagnosis of mild cognitive impairment (MCI, vertical dash lines, FIG. 9A). Importantly, the converter group had not been used in any of the analyses presented above, and thus presented a different (un-analyzed) set of research subjects. The longitudinal changes in plasma PHGDH levels were quantified in everyone using a simple linear regression of all the measured PHGDH levels of the individual (FIG. 9A). Considering most samples (38 samples) from the converter group were collected on or before the clinical diagnosis of cognitive impairment (78% of the total 49 samples), no data points from the regression analysis were left out. A simple analysis method was chosen over sophisticated methods to minimize the chances of over-fitting the data. Remarkably, the estimated linear regression coefficient ($\beta$) was positive in each of these 11 subjects (FIG. 9A), suggesting an increase of plasma PHGDH over time in every converter.

Next, it was checked whether the longitudinal changes ($\beta$s) were different between the converter group and the control group. The $\beta$s of the converters were greater than those of the controls (p-value <0.0026, t test) (FIG. 9B). The $\beta$s of the control group were not significantly different from 0 (p-value=0.38, t test; left plot, FIG. 9B), suggesting that plasma PHGDH was relatively stable over time in cognitively normal control subjects. Consistent to these results, a mixed model that accounted for sex and age reported a significant interaction between time and group (converter or control) (p-value=0.030, ANOVA), whereas the time effect was insignificant in the presence of the interaction term (p-value=0.922, ANOVA).

To call which research subject exhibited a longitudinal increase in PHGDH exRNA, a simple rule was designed, that is "$\beta$ minus the standard deviation of $\beta$ was greater than 0" (error bars above 0, FIG. 9C). Based on this rule, all 11 converters and 1 out of the 9 controls were called exhibiting longitudinal increases of PHGDH. Thus, the simple rule of "($\beta$-standard deviation of $\beta$)>0", which meant having a clear upward change, classified converters from controls with 100% sensitivity and 89% specificity in this cohort of elderly people. These data suggested that the longitudinal increase in plasma PHGDH was predictive of the clinical diagnosis of cognition impairment.

7.12 Example 11: Large Individual Variations in Post-Diagnosis Longitudinal Changes To further explore if PHGDH levels continue to rise following AD diagnosis or if they simply remain elevated, the longitudinal changes in the AD group were examined. The average $\beta$ of the AD group was not significantly different from 0 (p-value >0.99, t test; red box plot, FIG. 9B), suggesting the lack of a consistent direction of change. This was similar to the control group (left plot, FIG. 9B). However, the $\beta$s of the AD group were not clustered as tightly around 0 as those of the control group (middle vs. left, FIG. 9B), suggesting greater longitudinal variability of PHGDH exRNA after conversion of cognitive status. The $\beta$s of the converter group were greater than those of the AD group (p-value=0.022, t-test; right vs. middle, FIG. 9B), suggesting that a longitudinal increase in PHGDH exRNA was more consistently detected pre-symptomatically.

8. SEQUENCE LISTING

The present specification is being filed with a computer readable form (CRF) copy of the Sequence Listing. The CRF entitled 14637-001-228_SEQLIST.txt, which was created on Feb. 24, 2021 and is 4,970 bytes in size, which is incorporated herein by reference in its entirety.

9. REFERENCES

1. Ng, E. K., Tsui, N. B., Lam, N. Y., Chiu, R. W., Yu, S. C., Wong, S. C., Lo, E. S., Rainer, T. H., Johnson, P. J., and Lo, Y. M. (2002). Presence of filterable and nonfilterable mRNA in the plasma of cancer patients and healthy individuals. Clin Chem 48, 1212-1217.
2. Ng, E. K., Tsui, N. B., Lau, T. K., Leung, T. N., Chiu, R. W., Panesar, N. S., Lit, L. C., Chan, K. W., and Lo, Y. M. (2003). mRNA of placental origin is readily detectable in maternal plasma. Proc Natl Acad Sci USA 100, 4748-4753.
3. Garcia, J. M., Garcia, V., Pena, C., Dominguez, G., Silva, J., Diaz, R., Espinosa, P., Citores, M. J., Collado, M., and Bonilla, F. (2008). Extracellular plasma RNA from colon cancer patients is confined in a vesicle-like structure and is mRNA-enriched. RNA 14,
4. Freedman, J. E., Gerstein, M., Mick, E., Rozowsky, J., Levy, D., Kitchen, R., Das, S., Shah, R., Danielson, K., Beaulieu, L., et al. (2016). Diverse human extracellular RNAs are widely detected in human plasma. Nature communications 7, 11106.
5. Yeri, A., Courtright, A., Reiman, R., Carlson, E., Beecroft, T., Janss, A., Siniard, A., Richholt, R., Balak, C., Rozowsky, J., et al. (2017). Total Extracellular Small RNA Profiles from Plasma, Saliva, and Urine of Healthy Subjects. Sci Rep 7, 44061.
6. Yuan, T., Huang, X., Woodcock, M., Du, M., Dittmar, R., Wang, Y., Tsai, S., Kohli, M., Boardman, L., Patel, T., et al. (2016). Plasma extracellular RNA profiles in healthy and cancer patients. Sci Rep 6, 19413.
7. Murillo, O. D., Thistlethwaite, W., Rozowsky, J., Subramanian, S. L., Lucero, R., Shah, N., Jackson, A. R., Srinivasan, S., Chung, A., Laurent, C. D., et al. (2019). exRNA Atlas Analysis Reveals Distinct Extracellular RNA Cargo Types and Their Carriers Present across Human Biofluids. Cell 177, 463-477 e415.

8. Burgos, K., Malenica, I., Metpally, R., Courtright, A., Rakela, B., Beach, T., Shill, H., Adler, C., Sabbagh, M., Villa, S., et al. (2014). Profiles of extracellular miRNA in cerebrospinal fluid and serum from patients with Alzheimer's and Parkinson's diseases correlate with disease status and features of pathology. PLoS One 9, e94839.

9. Lee, M. Y., Baxter, D., Scherler, K., Kim, T. K., Wu, X., Abu-Amara, D., Flory, J., Yehuda, R., Marmar, C., Jett, M., et al. (2019). Distinct Profiles of Cell-Free MicroRNAs in Plasma of Veterans with Post-Traumatic Stress Disorder. J Clin Med 8.

10. Srinivasan, S., Yeri, A., Cheah, P. S., Chung, A., Danielson, K., De Hoff, P., Filant, J., Laurent, C. D., Laurent, L. D., Magee, R., et al. (2019). Small RNA Sequencing across Diverse Biofluids Identifies Optimal Methods for exRNA Isolation. Cell 177, 446-462 e416.

11. Zhou, Z., Wu, Q., Yan, Z., Zheng, H., Chen, C. J., Liu, Y., Qi, Z., Calandrelli, R., Chen, Z., Chien, S., et al. (2019). Extracellular RNA in a single droplet of human serum reflects physiologic and disease states. Proc Natl Acad Sci USA.

12. Yurkovich, J. T., and Hood, L. (2019). Blood Is a Window into Health and Disease. Clin Chem.

13. Momen-Heravi, F., Saha, B., Kodys, K., Catalano, D., Satishchandran, A., and Szabo, G. (2015). Increased number of circulating exosomes and their microRNA cargos are potential novel biomarkers in alcoholic hepatitis. J Transl Med 13, 261.

14. Max, K. E. A., Bertram, K., Akat, K. M., Bogardus, K. A., Li, J., Morozov, P., Ben-Dov, I. Z., Li, X., Weiss, Z. R., Azizian, A., et al. (2018). Human plasma and serum extracellular small RNA reference profiles and their clinical utility. Proc Natl Acad Sci USA 115, E5334-E5343.

15. Kunz, F., Kontopoulou, E., Reinhardt, K., Soldierer, M., Strachan, S., Reinhardt, D., and Thakur, B. K. (2019). Detection of AML-specific mutations in pediatric patient plasma using extracellular vesicle-derived RNA. Ann Hematol 98, 595-603.

16. Farrington, D. P. (1991). Longitudinal research strategies: advantages, problems, and prospects. J Am Acad Child Adolesc Psychiatry 30, 369-374.

17. Chen, R., Xia, L., Tu, K., Duan, M., Kukurba, K., Li-Pook-Than, J., Xie, D., and Snyder, M. (2018). Longitudinal personal DNA methylome dynamics in a human with a chronic condition. Nat Med 24, 1930-1939.

18. Jiang, C., Wang, X., Li, X., Inlora, J., Wang, T., Liu, Q., and Snyder, M. (2018). Dynamic Human Environmental Exposome Revealed by Longitudinal Personal Monitoring. Cell 175, 277-291 e231.

19. Zhou, W., Sailani, M. R., Contrepois, K., Zhou, Y., Ahadi, S., Leopold, S. R., Zhang, M. J., Rao, V., Avina, M., Mishra, T., et al. (2019). Longitudinal multi-omics of host-microbe dynamics in prediabetes. Nature 569, 663-671.

20. Lopez, J. P., Fiori, L. M., Cruceanu, C., Lin, R., Labonte, B., Cates, H. M., Heller, E. A., Vialou, V., Ku, S. M., Gerald, C., et al. (2017). MicroRNAs 146a/b-5 and 425-3p and 24-3p are markers of antidepressant response and regulate MAPK/Wnt-system genes. Nature communications 8, 15497.

21. Preische, O., Schultz, S. A., Apel, A., Kuhle, J., Kaeser, S. A., Barro, C., Graber, S., Kuder-Buletta, E., LaFougere, C., Laske, C., et al. (2019). Serum neurofilament dynamics predicts neurodegeneration and clinical progression in presymptomatic Alzheimer's disease. Nat Med 25, 277-283.

22. Nakamura, A., Kaneko, N., Villemagne, V. L., Kato, T., Doecke, J., Dore, V., Fowler, C., Li, Q. X., Martins, R., Rowe, C., et al. (2018). High performance plasma amyloid-beta biomarkers for Alzheimer's disease. Nature 554, 249-254.

23. Bacioglu, M., Maia, L. F., Preische, O., Schelle, J., Apel, A., Kaeser, S. A., Schweighauser, M., Eninger, T., Lambert, M., Pilotto, A., et al. (2016). Neurofilament Light Chain in Blood and CSF as Marker of Disease Progression in Mouse Models and in Neurodegenerative Diseases. Neuron 91, 494-496.

24. Weston, P. S. J., Poole, T., Ryan, N. S., Nair, A., Liang, Y., Macpherson, K., Druyeh, R., Malone, LB., Ahsan, R. L., Pemberton, H., et al. (2017). Serum neurofilament light in familial Alzheimer disease: A marker of early neurodegeneration. Neurology 89, 2167-2175.

25. Lin, Y. S., Lee, W. J., Wang, S. J., and Fuh, J. L. (2018). Levels of plasma neurofilament light chain and cognitive function in patients with Alzheimer or Parkinson disease. Sci Rep 8, 17368.

26. Mattsson, N., Andreasson, U., Zetterberg, H., Blennow, K., and Alzheimer's Disease Neuroimaging, I. (2017). Association of Plasma Neurofilament Light With Neurodegeneration in Patients With Alzheimer Disease. JAMA Neurol 74, 557-566.

27. Benedet, A. L., Ashton, N. J., Pascoal, T. A., Leuzy, A., Mathotaarachchi, S., Kang, M. S., Therriault, J., Savard, M., Chamoun, M., Scholl, M., et al. (2019). Plasma neurofilament light associates with Alzheimer's disease metabolic decline in amyloid-positive individuals. Alzheimers Dement (Amst) 11, 679-689.

28. Jia, L., Qiu, Q., Zhang, H., Chu, L., Du, Y., Zhang, J., Zhou, C., Liang, F., Shi, S., Wang, S., et al. (2019). Concordance between the assessment of Abeta42, T-tau, and P-T181-tau in peripheral blood neuronal-derived exosomes and cerebrospinal fluid. Alzheimers Dement 15, 1071-1080.

29. Schindler, S. E., Bollinger, J. G., Ovod, V., Mawuenyega, K. G., Li, Y., Gordon, B. A., Holtzman, D. M., Morris, J. C., Benzinger, T. L. S., Xiong, C., et al. (2019). High-precision plasma beta-amyloid 42/40 predicts current and future brain amyloidosis. Neurology.

30. Lim, C. Z. J., Zhang, Y., Chen, Y., Zhao, H., Stephenson, M. C., Ho, N. R. Y., Chen, Y., Chung, J., Reilhac, A., Loh, T. P., et al. (2019). Subtyping of circulating exosome-bound amyloid beta reflects brain plaque deposition. Nature communications 10, 1144.

31. Reiman, E. M., Langbaum, J. B., Fleisher, A. S., Caselli, R. J., Chen, K., Ayutyanont, N., Quiroz, Y. T., Kosik, K. S., Lopera, F., and Tariot, P. N. (2011). Alzheimer's Prevention Initiative: a plan to accelerate the evaluation of presymptomatic treatments. J Alzheimers Dis 26 Suppl 3, 321-329.

32. Frisoni, G. B., Boccardi, M., Barkhof, F., Blennow, K., Cappa, S., Chiotis, K., Demonet, J. F., Garibotto, V., Giannakopoulos, P., Gietl, A., et al. (2017). Strategic roadmap for an early diagnosis of Alzheimer's disease based on biomarkers. Lancet Neurol 16, 661-676.

33. Kapogiannis, D., Mustapic, M., Shardell, M. D., Berkowitz, S. T., Diehl, T. C., Spangler, R. D., Tran, J., Lazaropoulos, M. P., Chawla, S., Gulyani, S., et al. (2019). Association of Extracellular Vesicle Biomarkers With Alzheimer Disease in the Baltimore Longitudinal Study of Aging. JAMA Neurol.

34. Silverberg, N., Elliott, C., Ryan, L., Masliah, E., and Hodes, R. (2018). NIA commentary on the NIA-AA Research Framework: Towards a biological definition of Alzheimer's disease. Alzheimers Dement 14, 576-578.

35. Allen, M., Wang, X., Burgess, J. D., Watzlawik, J., Serie, D. J., Younkin, C. S., Nguyen, T., Malphrus, K. G., Lincoln, S., Carrasquillo, M. M., et al. (2018). Conserved brain myelination networks are altered in Alzheimer's and other neurodegenerative diseases. Alzheimers Dement 14, 352-366.

36. Sperling, R. A., Rentz, D. M., Johnson, K. A., Karlawish, J., Donohue, M., Salmon, D. P., and Aisen, P. (2014). The A4 study: stopping AD before symptoms begin? Sci Transl Med 6, 228fs213.

37. Readhead, B., Haure-Mirande, J. V., Funk, C. C., Richards, M. A., Shannon, P., Haroutunian, V., Sano, M., Liang, W. S., Beckmann, N. D., Price, N. D., et al. (2018). Multiscale Analysis of Independent Alzheimer's Cohorts Finds Disruption of Molecular, Genetic, and Clinical Networks by Human Herpesvirus. Neuron 99, 64-82 e67.

38. Liang, W. S., Dunckley, T., Beach, T. G., Grover, A., Mastroeni, D., Ramsey, K., Caselli, R. J., Kukull, W. A., McKeel, D., Morris, J. C., et al. (2008). Altered neuronal gene expression in brain regions differentially affected by Alzheimer's disease: a reference data set. Physiol Genomics 33, 240-256.

39. Wang, S., Qaisar, U., Yin, X., and Grammas, P. (2012). Gene expression profiling in Alzheimer's disease brain microvessels. J Alzheimers Dis 31, 193-205.

40. Patel, H., Dobson, R. J. B., and Newhouse, S. J. (2019). A Meta-Analysis of Alzheimer's Disease Brain Transcriptomic Data. J Alzheimers Dis 68, 1635-1656.

41. Mathys, H., Davila-Velderrain, J., Peng, Z., Gao, F., Mohammadi, S., Young, J. Z., Menon, M., He, L., Abdurrob, F., Jiang, X., et al. (2019). Single-cell transcriptomic analysis of Alzheimer's disease. Nature 570, 332-337.

42. Huynh, R. A., and Mohan, C. (2017). Alzheimer's Disease: Biomarkers in the Genome, Blood, and Cerebrospinal Fluid. Front Neurol 8, 102.

43. Guo, C., Jeong, H. H., Hsieh, Y. C., Klein, H. U., Bennett, D. A., De Jager, P. L., Liu, Z., and Shulman, J. M. (2018). Tau Activates Transposable Elements in Alzheimer's Disease. Cell Rep 23, 2874-2880.

44. Li, W., Prazak, L., Chatterjee, N., Gruninger, S., Krug, L., Theodorou, D., and Dubnau, J. (2013). Activation of transposable elements during aging and neuronal decline in *Drosophila*. Nat Neurosci 16, 529-531.

45. Li, W., Jin, Y., Prazak, L., Hammell, M., and Dubnau, J. (2012). Transposable elements in TDP-43-mediated neurodegenerative disorders. PLoS One 7, e44099.

46. Sun, W., Samimi, H., Gamez, M., Zare, H., and Frost, B. (2018). Pathogenic tau-induced piRNA depletion promotes neuronal death through transposable element dysregulation in neurodegenerative tauopathies. Nat Neurosci 21, 1038-1048.

47. Pinero, J., Ramirez-Anguita, J. M., Sauch-Pitarch, J., Ronzano, F., Centeno, E., Sanz, F., and Furlong, L. I. (2019). The DisGeNET knowledge platform for disease genomics: 2019 update. Nucleic Acids Res.

48. Barbash, S., Garfinkel, B. P., Maoz, R., Simchovitz, A., Nadorp, B., Guffanti, A., Bennett, E. R., Nadeau, C., Turk, A., Paul, L., et al. (2017). Alzheimer's brains show inter-related changes in RNA and lipid metabolism. Neurobiol Dis 106, 1-13.

49. Sato, N., and Morishita, R. (2015). The roles of lipid and glucose metabolism in modulation of beta-amyloid, tau, and neurodegeneration in the pathogenesis of Alzheimer disease. Front Aging Neurosci 7, 199.

50. Hodes, R. J., and Buckholtz, N. (2016). Accelerating Medicines Partnership: Alzheimer's Disease (AMP-AD) Knowledge Portal Aids Alzheimer's Drug Discovery through Open Data Sharing. Expert Opin Ther Targets 20, 389-391.

51. De Jager, P. L., Ma, Y., McCabe, C., Xu, J., Vardaraj an, B. N., Felsky, D., Klein, H. U., White, C. C., Peters, M. A., Lodgson, B., et al. (2018). A multi-omic atlas of the human frontal cortex for aging and Alzheimer's disease research. Sci Data 5, 180142.

52. Yang, R. Y., Quan, J., Sodaei, R., Aguet, F., Segre, A. V., Allen, J. A., Lanz, T. A., Reinhart, V., Crawford, M., Hasson, S., et al. (2018). A systematic survey of human tissue-specific gene expression and splicing reveals new opportunities for therapeutic target identification and evaluation. 311563.

53. Hondius, D. C., van Nierop, P., Li, K. W., Hoozemans, J. J., van der Schors, R. C., van Haastert, E. S., van der Vies, S. M., Rozemuller, A. J., and Smit, A. B. (2016). Profiling the human hippocampal proteome at all pathologic stages of Alzheimer's disease. Alzheimers Dement 12, 654-668.

54. Seyfried, N. T., Dammer, E. B., Swamp, V., Nandakumar, D., Duong, D. M., Yin, L., Deng, Q., Nguyen, T., Hales, C. M., Wingo, T., et al. (2017). A Multi-network Approach Identifies Protein-Specific Co-expression in Asymptomatic and Symptomatic Alzheimer's Disease. Cell Syst 4, 60-72 e64.

55. Ping, L., Duong, D. M., Yin, L., Gearing, M., Lah, J. J., Levey, A. I., and Seyfried, N. T. (2018). Global quantitative analysis of the human brain proteome in Alzheimer's and Parkinson's Disease. Sci Data 5, 180036.

56. Tsang, J. C. H., Vong, J. S. L., Ji, L., Poon, L. C. Y., Jiang, P., Lui, K. O., Ni, Y. B., To, K. F., Cheng, Y. K. Y., Chiu, R. W. K., et al. (2017). Integrative single-cell and cell-free plasma RNA transcriptomics elucidates placental cellular dynamics. Proc Natl Acad Sci USA 114, E7786-E7795.

57. Absinta, M., Ha, S. K., Nair, G., Sati, P., Luciano, N. J., Palisoc, M., Louveau, A., Zaghloul, K. A., Pittaluga, S., Kipnis, J., et al. (2017). Human and nonhuman primate meninges harbor lymphatic vessels that can be visualized noninvasively by MM. Elife 6.

58. Da Mesquita, S., Louveau, A., Vaccari, A., Smirnov, I., Cornelison, R. C., Kingsmore, K. M., Contarino, C., Onengut-Gumuscu, S., Farber, E., Raper, D., et al. (2018). Functional aspects of meningeal lymphatics in ageing and Alzheimer's disease. Nature 59. Alvarez-Erviti, L., Seow, Y., Yin, H., Betts, C., Lakhal, S., and Wood, M. J. (2011). Delivery of siRNA to the mouse brain by systemic injection of targeted exosomes. Nature biotechnology 29, 341-345.

60. van de Haar, H. J., Burgmans, S., Jansen, J. F., van Osch, M. J., van Buchem, M. A., Muller, M., Hofman, P. A., Verhey, F. R., and Backes, W. H. (2016). Blood-Brain Barrier Leakage in Patients with Early Alzheimer Disease. Radiology 281, 527-535.

61. Sweeney, M. D., Sagare, A. P., and Zlokovic, B. V. (2018). Blood-brain barrier breakdown in Alzheimer disease and other neurodegenerative disorders. Nat Rev Neurol 14, 133-150.

62. Chen, X. Q., and Mobley, W. C. (2019). Alzheimer Disease Pathogenesis: Insights From Molecular and Cellular Biology Studies of Oligomeric Abeta and Tau Species. Front Neurosci 13, 659.

63. Zhou, Z., Wu, Q., Yan, Z., Zheng, H., Chen, C., Liu, Y., Qi, Z., Calandrelli, R., Chen, Z., Chien, S., et al. (2019). Extracellular RNA in a single droplet of human serum reflects physiologic and disease states. Proc Natl Acad Sci USA In press.

64. Zhou, Z., Wu, Q., Yan, Z., Zheng, H., Chen, C. J., Liu, Y., Qi, Z., Calandrelli, R., Chen, Z., Chien, S., et al. (2019). Extracellular RNA in a single droplet of human serum reflects physiologic and disease states. Proc Natl Acad Sci USA 116, 19200-19208.

65. Yang, J. H., Wada, A., Yoshida, K., Miyoshi, Y., Sayano, T., Esaki, K., Kinoshita, M. O., Tomonaga, S., Azuma, N., Watanabe, M., et al. (2010). Brain-specific Phgdh deletion reveals a pivotal role for L-serine biosynthesis in controlling the level of D-serine, an N-methyl-D-aspartate receptor co-agonist, in adult brain. The Journal of biological chemistry 285, 41380-41390.

66. Zhu, S., Stein, R. A., Yoshioka, C., Lee, C. H., Goehring, A., McHaourab, H. S., and Gouaux, E. (2016). Mechanism of NMDA Receptor Inhibition and Activation. Cell 165, 704-714.

67. Le Bail, M., Martineau, M., Sacchi, S., Yatsenko, N., Radzishevsky, I., Conrod, S., Ait Ouares, K., Wolosker, H., Pollegioni, L., Billard, J. M., et al. (2015). Identity of the NMDA receptor coagonist is synapse specific and developmentally regulated in the hippocampus. Proc Natl Acad Sci USA 112, E204-213.

68. Hynd, M. R., Scott, H. L., and Dodd, P. R. (2004). Glutamate-mediated excitotoxicity and neurodegeneration in Alzheimer's disease. Neurochem Int 45, 583-595.

69. Ehmsen, J. T., Ma, T. M., Sason, H., Rosenberg, D., Ogo, T., Furuya, S., Snyder, S. H., and Wolosker, H. (2013). D-serine in glia and neurons derives from 3-phosphoglycerate dehydrogenase. J Neurosci 33, 12464-12469.

70. Hashimoto, A., Nishikawa, T., Oka, T., and Takahashi, K. (1993). Endogenous D-serine in rat brain: N-methyl-D-aspartate receptor-related distribution and aging. J Neurochem 60, 783-786.

71. Katsuki, H., Watanabe, Y., Fujimoto, S., Kume, T., and Akaike, A. (2007). Contribution of endogenous glycine and d-serine to excitotoxic and ischemic cell death in rat cerebrocortical slice cultures. Life Sci 81, 740-749.

72. Sasabe, J., Chiba, T., Yamada, M., Okamoto, K., Nishimoto, I., Matsuoka, M., and Aiso, S. (2007). D-serine is a key determinant of glutamate toxicity in amyotrophic lateral sclerosis. EMBO J 26, 4149-4159.

73. Perez, E. J., Tapanes, S. A., Loris, Z. B., Balu, D. T., Sick, T. J., Coyle, J. T., and Liebl, D. J. (2017). Enhanced astrocytic d-serine underlies synaptic damage after traumatic brain injury. J Clin Invest 127, 3114-3125.

74. Madeira, C., Lourenco, M. V., Vargas-Lopes, C., Suemoto, C. K., Brandao, C. O., Reis, T., Leite, R. E., Laks, J., Jacob-Filho, W., Pasqualucci, C. A., et al. (2015). d-serine levels in Alzheimer's disease: implications for novel biomarker development. Transl Psychiatry 5, e561.

75. Mustafa, A. K., Ahmad, A. S., Zeynalov, E., Gazi, S. K., Sikka, G., Ehmsen, J. T., Barrow, R. K., Coyle, J. T., Snyder, S. H., and Dore, S. (2010). Serine racemase deletion protects against cerebral ischemia and excitotoxicity. J Neurosci 30, 1413-1416.

76. Sasabe, J., Miyoshi, Y., Suzuki, M., Mita, M., Konno, R., Matsuoka, M., Hamase, K., and Aiso, S. (2012). D-amino acid oxidase controls motoneuron degeneration through D-serine. Proc Natl Acad Sci USA 109, 627-632.

77. Zott, B., Simon, M. M., Hong, W., Unger, F., Chen-Engerer, H. J., Frosch, M. P., Sakmann, B., Walsh, D. M., and Konnerth, A. (2019). A vicious cycle of beta amyloid-dependent neuronal hyperactivation. Science 365, 559-565.

78. Witt, A., Macdonald, N., and Kirkpatrick, P. (2004). Memantine hydrochloride. Nature reviews. Drug discovery 3, 109-110.

79. McShane, R., Westby, M. J., Roberts, E., Minakaran, N., Schneider, L., Farrimond, L. E., Maayan, N., Ware, J., and Debarros, J. (2019). Memantine for dementia. Cochrane Database Syst Rev 3, CD003154.

80. Li, W., Lee, M. H., Henderson, L., Tyagi, R., Bachani, M., Steiner, J., Campanac, E., Hoffman, D. A., von Geldern, G., Johnson, K., et al. (2015). Human endogenous retrovirus-K contributes to motor neuron disease. Sci Transl Med 7, 307ra153.

81. Liu, E. Y., Russ, J., Cali, C. P., Phan, J. M., Amlie-Wolf, A., and Lee, E. B. (2019). Loss of Nuclear TDP-43 Is Associated with Decondensation of LINE Retrotransposons. Cell Rep 27, 1409-1421 e1406.

82. Balu, D. T. (2016). The NMDA Receptor and Schizophrenia: From Pathophysiology to Treatment. Adv Pharmacol 76, 351-382.

83. Spalloni, A., Nutini, M., and Longone, P. (2013). Role of the N-methyl-d-aspartate receptors complex in amyotrophic lateral sclerosis. Biochim Biophys Acta 1832, 312-322.

84. Ghasemi, M., and Schachter, S. C. (2011). The NMDA receptor complex as a therapeutic target in epilepsy: a review. Epilepsy Behav 22, 617-640.

85. Tomek, S. E., Lacrosse, A. L., Nemirovsky, N. E., and Olive, M. F. (2013). NMDA Receptor Modulators in the Treatment of Drug Addiction. Pharmaceuticals (Basel) 6, 251-268.

86. Chen, J., Ma, Y., Fan, R., Yang, Z., and Li, M. D. (2018). Implication of Genes for the N-Methyl-D-Aspartate (NMDA) Receptor in Substance Addictions. Mol Neurobiol 55, 7567-7578.

87. Bolger, A. M., Lohse, M., and Usadel, B. J. B. (2014). Trimmomatic: a flexible trimmer for Illumina sequence data. 30, 2114-2120.

88. Jeong, H.-H., Yalamanchili, H. K., Guo, C., Shulman, J. M., and Liu, Z. (2018). An ultra-fast and scalable quantification pipeline for transposable elements from next generation sequencing data. In Pac. Symp. Biocomput, Volume 23. (World Scientific), pp. 168-179.

89. Liao, Y., Smyth, G. K., and Shi, W. J. B. (2013). featureCounts: an efficient general purpose program for assigning sequence reads to genomic features. 30, 923-930.

90. Rozowsky, J., Kitchen, R. R., Park, J. J., Galeev, T. R., Diao, J., Warrell, J., Thistlethwaite, W., Subramanian, S. L., Milosavljevic, A., and Gerstein, M. (2019). exceRpt: A Comprehensive Analytic Platform for Extracellular RNA Profiling. Cell Syst 8, 352-357 e353.

91. Team, R. C. (2013). R: A language and environment for statistical computing.

92. Bates, D., Machler, M., Bolker, B. M., and Walker, S. C. (2015). Fitting Linear Mixed-Effects Models Using lme4. J Stat Softw 67, 1-48.

What is claimed is:

1. A method of managing, or treating a neuronal disorder associated with neuro-excitotoxicity in a subject, comprising
(a) monitoring the expression level of phosphoglycerate dehydrogenase (PHGDH) in the subject over an observation period of time; and
(b) administering to the subject an effective amount of a therapy for managing or treating the neuronal disorder, if the expression level of PHGDH is increased during the observation period;
wherein the neuronal disorder is managed or treated in the subject, and the monitoring further comprises:
providing a series of samples taken from the subject at sequential time points before or during the observation period;
measuring the expression level of PHGDH using the series of samples; and
determining a longitudinal trend in the expression level of PHGDH.

2. The method of claim 1, wherein the therapy comprises at least one NMDA receptor antagonist.

3. The method of claim 2, wherein the NMDA receptor antagonist is memantine.

4. The method of claim 1, wherein the therapy comprises at least one agent inhibiting in vivo production of glycine and/or serine in the subject.

5. The method of claim 4, wherein the agent inhibiting in vivo production of glycine and/or serine is a PHGDH inhibitor.

6. The method of claim 1, wherein the therapy comprises at least one agent inhibiting in vivo transportation of glycine and/or serine to excitatory synapses in the subject.

7. The method of claim 1, further comprising
(c) extending the observation period for an extended period, if the expression level of PHGDH is not increased during the observation period; optionally wherein the extended period is at least 1 month; optionally wherein the method further comprises measuring the expression level every 6 months during the extended period.

8. The method of claim 1, wherein the observation period is at least 1 month.

9. The method of claim 1, wherein the subject is asymptomatic of the neuronal disorder at the beginning or during the observation period.

10. A method of managing or treating a neuronal disorder associated with neuro-excitotoxicity in a subject who is under an ongoing first therapy for the neuronal disorder, comprising
(a) monitoring the expression level of phosphoglycerate dehydrogenase (PHGDH) in the subject over an observation period of time;
(b) administering a second therapy to the subject, if the expression level of PHGDH is increased during the observation period; wherein the first therapy and second therapy are different; and
(c) ceasing the ongoing first therapy and administering a third therapy to the subject, if the expression level of PHGDH is not increased during the observation period;
wherein the neuronal disorder is managed or treated in the subject, the first therapy comprises at least one NMDA receptor antagonist, and the third therapy does not comprise any NMDA receptor antagonist.

11. The method of claim 10, wherein the step (c) selected from (ii) further comprises extending the observation period for an extended period.

12. A method of diagnosing a neuronal disorder associated with neuro-excitotoxicity in a subject, comprising
(a) monitoring the expression level of phosphoglycerate dehydrogenase (PHGDH) in the subject over an observation period of time; and

US 12,636,264 B2

35

(b) classifying the subject as having the neuronal disorder or at a high risk of developing the neuronal disorder, if the expression level of PHGDH is increased during the observation period; or (c) classifying the subject as having a low risk of developing the neuronal disorder, if the expression level of PHGDH is increased during the observation period;

wherein the neuronal disorder is diagnosed in the subject, monitoring the expression level of PHGDH is performed by measuring the amount of extracellular RNA (exRNA) produced from expression of PHGDH in the subject, and the exRNA is produced from transcription of the PHGDH gene.

13. The method of claim 12, wherein the risk is a risk of developing the neuronal disorder in less than 5 years, or the risk is a risk of having the onset of symptom for the neuronal disorder-in less than.

14. The method of claim 1, wherein (a) at least one of the series of samples is (i) a sample preserved from a time point before the observation period; (ii) a whole blood sample, a plasma sample, a serum sample, a saliva sample, a cell culture media sample, a urine sample, an amniotic fluid sample, a mucus sample, a semen sample, a vaginal fluid sample, a sputum sample, a cerebrospinal fluid sample, a lymphatic fluid sample, an ocular fluid sample, a sweat sample, or a stool sample; or (iii) has a liquid volume of less than or equal to about 100 µl, about 50 µl, about 5 µl, or about 1 µl; and (b) extending the observation period comprises taking at least one additional sample from the subject and measuring expression level of PHGDH using said sample.

15. The method of claim 1, wherein the neuro-excitotoxicity is resulted from overexcitation of an excitatory synaptic receptor upon binding of glycine and/or serine to the excitatory synaptic receptor.

16. The method of claim 1, wherein the neuronal disorder is Alzheimer's disease, schizophrenia, ALS, epilepsy, or drug addiction.

* * * * *

SEQUENCE LISTING

<160> NUMBER OF SEQ ID NOS: 1

<210> SEQ ID NO 1
<211> LENGTH: 533
<212> TYPE: PRT
<213> ORGANISM: Homo sapiens
<220> FEATURE:
<223> OTHER INFORMATION: Human PHGDH amino acid sequence

<400> SEQUENCE: 1

Met Ala Phe Ala Asn Leu Arg Lys Val Leu Ile Ser Asp Ser Leu Asp
1               5                   10                  15

Pro Cys Cys Arg Lys Ile Leu Gln Asp Gly Gly Leu Gln Val Val Glu
            20                  25                  30

Lys Gln Asn Leu Ser Lys Glu Glu Leu Ile Ala Glu Leu Gln Asp Cys
        35                  40                  45

Glu Gly Leu Ile Val Arg Ser Ala Thr Lys Val Thr Ala Asp Val Ile
        50                  55                  60

Asn Ala Ala Glu Lys Leu Gln Val Val Gly Arg Ala Gly Thr Gly Val
65                  70                  75                  80

Asp Asn Val Asp Leu Glu Ala Ala Thr Arg Lys Gly Ile Leu Val Met
                85                  90                  95

Asn Thr Pro Asn Gly Asn Ser Leu Ser Ala Ala Glu Leu Thr Cys Gly
            100                 105                 110

Met Ile Met Cys Leu Ala Arg Gln Ile Pro Gln Ala Thr Ala Ser Met
            115                 120                 125

Lys Asp Gly Lys Trp Glu Arg Lys Lys Phe Met Gly Thr Glu Leu Asn
        130                 135                 140

Gly Lys Thr Leu Gly Ile Leu Gly Leu Gly Arg Ile Gly Arg Glu Val
145                 150                 155                 160

Ala Thr Arg Met Gln Ser Phe Gly Met Lys Thr Ile Gly Tyr Asp Pro
                165                 170                 175

Ile Ile Ser Pro Glu Val Ser Ala Ser Phe Gly Val Gln Gln Leu Pro
            180                 185                 190

Leu Glu Glu Ile Trp Pro Leu Cys Asp Phe Ile Thr Val His Thr Pro
            195                 200                 205

Leu Leu Pro Ser Thr Thr Gly Leu Leu Asn Asp Asn Thr Phe Ala Gln
        210                 215                 220

Cys Lys Lys Gly Val Arg Val Val Asn Cys Ala Arg Gly Gly Ile Val
225                 230                 235                 240

Asp Glu Gly Ala Leu Leu Arg Ala Leu Gln Ser Gly Gln Cys Ala Gly
                245                 250                 255

Ala Ala Leu Asp Val Phe Thr Glu Glu Pro Pro Arg Asp Arg Ala Leu
            260                 265                 270

Val Asp His Glu Asn Val Ile Ser Cys Pro His Leu Gly Ala Ser Thr
        275                 280                 285

Lys Glu Ala Gln Ser Arg Cys Gly Glu Glu Ile Ala Val Gln Phe Val
        290                 295                 300

Asp Met Val Lys Gly Lys Ser Leu Thr Gly Val Val Asn Ala Gln Ala
305                 310                 315                 320

Leu Thr Ser Ala Phe Ser Pro His Thr Lys Pro Trp Ile Gly Leu Ala
                325                 330                 335

Glu Ala Leu Gly Thr Leu Met Arg Ala Trp Ala Gly Ser Pro Lys Gly
            340                 345                 350

Thr Ile Gln Val Ile Thr Gln Gly Thr Ser Leu Lys Asn Ala Gly Asn

-continued

```
           355                    360                    365

Cys Leu Ser Pro Ala Val Ile Val Gly Leu Leu Lys Glu Ala Ser Lys
        370                    375                    380

Gln Ala Asp Val Asn Leu Val Asn Ala Lys Leu Leu Val Lys Glu Ala
385                    390                    395                    400

Gly Leu Asn Val Thr Thr Ser His Ser Pro Ala Ala Pro Gly Glu Gln
                    405                    410                    415

Gly Phe Gly Glu Cys Leu Leu Ala Val Ala Leu Ala Gly Ala Pro Tyr
                420                    425                    430

Gln Ala Val Gly Leu Val Gln Gly Thr Thr Pro Val Leu Gln Gly Leu
            435                    440                    445

Asn Gly Ala Val Phe Arg Pro Glu Val Pro Leu Arg Arg Asp Leu Pro
        450                    455                    460

Leu Leu Leu Phe Arg Thr Gln Thr Ser Asp Pro Ala Met Leu Pro Thr
465                    470                    475                    480

Met Ile Gly Leu Leu Ala Glu Ala Gly Val Arg Leu Leu Ser Tyr Gln
                485                    490                    495

Thr Ser Leu Val Ser Asp Gly Glu Thr Trp His Val Met Gly Ile Ser
                500                    505                    510

Ser Leu Leu Pro Ser Leu Glu Ala Trp Lys Gln His Val Thr Glu Ala
            515                    520                    525

Phe Gln Phe His Phe
        530
```